(12) United States Patent
Stone et al.

(10) Patent No.: US 9,414,833 B2
(45) Date of Patent: Aug. 16, 2016

(54) SOFT TISSUE REPAIR ASSEMBLY AND ASSOCIATED METHOD

(71) Applicant: Biomet Sports Medicine, LLC, Warsaw, IN (US)

(72) Inventors: Kevin T. Stone, Winona Lake, IN (US); Troy M. Walters, Plymouth, IN (US); Andrew Holst, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 409 days.

(21) Appl. No.: 13/767,401

(22) Filed: Feb. 14, 2013

(65) Prior Publication Data

US 2013/0158601 A1 Jun. 20, 2013

Related U.S. Application Data

(60) Continuation of application No. 12/828,977, filed on Jul. 1, 2010, now Pat. No. 8,409,253, which is a division of application No. 11/347,661, filed on Feb. 3, 2006, now Pat. No. 7,749,250.

(51) Int. Cl.
*A61B 17/04* (2006.01)
*A61B 17/06* (2006.01)
*A61B 17/064* (2006.01)

(52) U.S. Cl.
CPC ......... *A61B 17/0401* (2013.01); *A61B 17/0469* (2013.01); *A61B 17/0482* (2013.01);
(Continued)

(58) Field of Classification Search
CPC ........... A61B 17/0401; A61B 17/0469; A61B 17/0482; A61B 17/06166; A61B 17/0487; A61B 2017/0404; A61B 2017/0406; A61B 2017/0475; A61B 2017/0496; A61B 2017/06052; A61B 2017/0646; A61B 2017/042; A61B 2017/0458; A61B 2017/0414; A61B 2017/0409; A61B 2017/0445; A61B 2017/0464; A61B 2017/06185; A61B 2017/0618
USPC .................. 606/213, 215, 216, 232, 233; 623/13.15, 13.11
See application file for complete search history.

(56) References Cited

U.S. PATENT DOCUMENTS 64,499 A 5/1867 Daubert
65,499 A 6/1867 Miller
(Continued)

FOREIGN PATENT DOCUMENTS

AU 4957264 3/1966
AU 440266 10/1967
(Continued)

OTHER PUBLICATIONS

International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
(Continued)

*Primary Examiner* — Dianne Dornbusch
(74) *Attorney, Agent, or Firm* — Schwegman Lundberg & Woessner, P.A.

(57) ABSTRACT

A soft tissue repair assembly. The assembly includes a flexible member having first and second ends, and a strand passing through the flexible member. The strand has first and second strand ends extending through the flexible member, such that pulling at least one of the first and second strand ends changes the flexible member from a first shape suitable for insertion through soft tissue to a second shape suitable for securely lodging the soft tissue repair assembly relative to soft tissue.

25 Claims, 11 Drawing Sheets

(52) U.S. Cl.
CPC . *A61B2017/0404* (2013.01); *A61B 2017/0406* (2013.01); *A61B 2017/0409* (2013.01); *A61B 2017/0475* (2013.01); *A61B 2017/0496* (2013.01); *A61B 2017/0646* (2013.01); *A61B 2017/06052* (2013.01)

(56) References Cited

U.S. PATENT DOCUMENTS

| | | |
|---|---|---|
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,379,629 A | 7/1945 | Eweson |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,223,083 A | 12/1965 | Cobey |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,786,801 A | 1/1974 | Sartorius |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,896,810 A | 7/1975 | Akiyama |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |

(56) References Cited

U.S. PATENT DOCUMENTS

| | | | |
|---|---|---|---|
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes et al. |
| 4,144,876 | A | 3/1979 | DeLeo |
| 4,146,022 | A | 3/1979 | Johnson et al. |
| 4,149,277 | A | 4/1979 | Bokros |
| 4,157,714 | A | 6/1979 | Foltz et al. |
| 4,158,250 | A | 6/1979 | Ringwald |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |
| 4,207,627 | A | 6/1980 | Cloutier |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser et al. |
| 4,275,490 | A | 6/1981 | Bivins |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,302,397 | A | 11/1981 | Frainier et al. |
| 4,307,723 | A | 12/1981 | Finney |
| 4,312,337 | A | 1/1982 | Donohue |
| 4,316,469 | A | 2/1982 | Kapitanov et al. |
| 4,326,531 | A | 4/1982 | Shimonaka et al. |
| 4,344,193 | A | 8/1982 | Kenny |
| 4,345,601 | A | 8/1982 | Fukuda |
| 4,349,027 | A | 9/1982 | DiFrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,489,464 | A | 12/1984 | Massari et al. |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'Holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs et al. |
| 4,570,623 | A | 2/1986 | Ellison et al. |
| 4,573,844 | A | 3/1986 | Smith |
| 4,576,608 | A | 3/1986 | Homsy |
| 4,584,722 | A * | 4/1986 | Levy et al. ................ 623/13.15 |
| 4,587,963 | A | 5/1986 | Leibinger et al. |
| 4,590,928 | A | 5/1986 | Hunt et al. |
| 4,595,007 | A | 6/1986 | Mericle |
| 4,596,249 | A | 6/1986 | Freda et al. |
| 4,597,766 | A | 7/1986 | Hilal et al. |
| 4,602,635 | A | 7/1986 | Mulhollan et al. |
| 4,602,636 | A | 7/1986 | Noiles |
| 4,604,997 | A | 8/1986 | De Bastiani et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | McGarry et al. |
| 4,632,100 | A | 12/1986 | Somers et al. |
| 4,635,637 | A | 1/1987 | Schreiber |
| 4,636,121 | A | 1/1987 | Miller |
| 4,641,652 | A | 2/1987 | Hutterer et al. |
| 4,649,916 | A | 3/1987 | Frimberger |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,777 | A | 4/1987 | Dunn et al. |
| 4,662,068 | A | 5/1987 | Polonsky |
| 4,667,662 | A | 5/1987 | Titone et al. |
| 4,667,675 | A | 5/1987 | Davis |
| 4,669,473 | A | 6/1987 | Richards et al. |
| 4,683,895 | A | 8/1987 | Pohndorf |
| 4,688,561 | A | 8/1987 | Reese |
| 4,690,169 | A | 9/1987 | Jobe |
| 4,696,300 | A | 9/1987 | Anderson |
| 4,705,040 | A | 11/1987 | Mueller et al. |
| 4,708,132 | A | 11/1987 | Silvestrini |
| 4,714,475 | A | 12/1987 | Grundei et al. |
| 4,716,893 | A | 1/1988 | Fischer et al. |
| 4,719,671 | A | 1/1988 | Ito et al. |
| 4,719,917 | A | 1/1988 | Barrows et al. |
| 4,723,540 | A | 2/1988 | Gilmer, Jr. |
| 4,724,839 | A | 2/1988 | Bedi et al. |
| 4,728,332 | A | 3/1988 | Albrektsson |
| 4,736,746 | A | 4/1988 | Anderson |
| 4,738,255 | A | 4/1988 | Goble et al. |
| 4,739,751 | A | 4/1988 | Sapega et al. |
| 4,741,330 | A | 5/1988 | Hayhurst |
| 4,741,336 | A | 5/1988 | Failla et al. |
| 4,744,353 | A | 5/1988 | McFarland |
| 4,744,793 | A | 5/1988 | Parr et al. |
| 4,750,492 | A | 6/1988 | Jacobs |
| 4,751,922 | A | 6/1988 | DiPietropolo |
| 4,760,843 | A | 8/1988 | Fischer et al. |
| 4,760,844 | A | 8/1988 | Kyle |
| 4,760,848 | A | 8/1988 | Hasson |
| 4,770,663 | A | 9/1988 | Hanslik et al. |
| 4,772,261 | A | 9/1988 | Von Hoff et al. |
| 4,772,286 | A | 9/1988 | Goble et al. |
| 4,773,910 | A | 9/1988 | Chen et al. |
| 4,775,380 | A | 10/1988 | Seedhom et al. |
| 4,776,328 | A | 10/1988 | Frey et al. |
| 4,781,190 | A | 11/1988 | Lee et al. |
| 4,784,126 | A | 11/1988 | Hourahane |
| 4,787,882 | A | 11/1988 | Claren et al. |
| 4,790,297 | A | 12/1988 | Luque et al. |
| 4,790,850 | A * | 12/1988 | Dunn et al. ................ 623/13.19 |
| 4,793,363 | A | 12/1988 | Ausherman et al. |
| 4,809,695 | A | 3/1989 | Gwathmey et al. |
| 4,813,406 | A | 3/1989 | Ogle, II |
| 4,823,780 | A | 4/1989 | Odensten et al. |
| 4,823,794 | A | 4/1989 | Pierce |
| 4,828,562 | A | 5/1989 | Kenna |
| 4,832,026 | A | 5/1989 | Jones |
| 4,834,098 | A | 5/1989 | Jones |
| 4,838,282 | A | 6/1989 | Strasser et al. |
| 4,841,960 | A | 6/1989 | Garner |
| 4,846,835 | A | 7/1989 | Grande |
| 4,851,005 | A | 7/1989 | Hunt et al. |
| 4,858,601 | A | 8/1989 | Glisson |
| 4,858,603 | A | 8/1989 | Clemow et al. |
| 4,858,608 | A | 8/1989 | McQuilkin et al. |
| 4,860,513 | A | 8/1989 | Whitman |

(56) References Cited

U.S. PATENT DOCUMENTS

| | | |
|---|---|---|
| 4,863,383 A | 9/1989 | Grafelmann et al. |
| 4,870,957 A | 10/1989 | Goble et al. |
| 4,872,450 A | 10/1989 | Austad |
| 4,873,976 A | 10/1989 | Schreiber |
| 26,501 A | 12/1989 | Kendrick et al. |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 445,875 A | 2/1991 | Brickell |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,080,050 A | 1/1992 | Dale |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A * | 12/1992 | Fluckiger et al. .......... 623/13.16 |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |

(56) References Cited

U.S. PATENT DOCUMENTS

| | | | |
|---|---|---|---|
| 5,314,429 A | 5/1994 | Goble | |
| 5,318,566 A | 6/1994 | Miller | |
| 5,318,575 A | 6/1994 | Chesterfield et al. | |
| 5,318,577 A | 6/1994 | Li | |
| 5,318,578 A | 6/1994 | Hasson | |
| 5,320,115 A | 6/1994 | Kenna | |
| 5,320,626 A | 6/1994 | Schmieding | |
| 5,320,633 A | 6/1994 | Allen et al. | |
| 5,324,308 A | 6/1994 | Pierce | |
| 5,330,489 A | 7/1994 | Green et al. | |
| 5,333,625 A | 8/1994 | Klein | |
| 5,334,204 A | 8/1994 | Clewett et al. | |
| 5,336,229 A | 8/1994 | Noda | |
| 5,336,231 A | 8/1994 | Adair | |
| 5,336,240 A | 8/1994 | Metzler et al. | |
| 5,339,870 A | 8/1994 | Green et al. | |
| 5,342,369 A | 8/1994 | Harryman, II | |
| 5,346,462 A | 9/1994 | Barber | |
| 5,350,380 A | 9/1994 | Goble et al. | |
| RE34,762 E | 10/1994 | Goble et al. | |
| 5,354,292 A | 10/1994 | Braeuer et al. | |
| 5,354,298 A | 10/1994 | Lee et al. | |
| 5,354,299 A | 10/1994 | Coleman | |
| 5,356,412 A | 10/1994 | Golds et al. | |
| 5,356,413 A | 10/1994 | Martins et al. | |
| 5,356,417 A | 10/1994 | Golds | |
| 5,358,511 A | 10/1994 | Gatturna et al. | |
| 5,360,431 A | 11/1994 | Puno et al. | |
| 5,362,294 A | 11/1994 | Seitzinger | |
| 5,362,911 A | 11/1994 | Cevasco | |
| 5,364,400 A | 11/1994 | Rego, Jr. et al. | |
| 5,366,461 A | 11/1994 | Blasnik | |
| 5,368,599 A | 11/1994 | Hirsch et al. | |
| 5,370,661 A | 12/1994 | Branch | |
| 5,370,662 A | 12/1994 | Stone et al. | |
| 5,372,146 A | 12/1994 | Branch | |
| 5,372,604 A | 12/1994 | Trott | |
| 5,372,821 A | 12/1994 | Badylak et al. | |
| 5,374,268 A | 12/1994 | Sander | |
| 5,374,269 A | 12/1994 | Rosenberg | |
| 5,379,492 A | 1/1995 | Glesser | |
| 5,383,878 A | 1/1995 | Roger et al. | |
| 5,383,904 A | 1/1995 | Totakura et al. | |
| 5,385,567 A | 1/1995 | Goble | |
| 5,391,171 A | 2/1995 | Schmieding | |
| 5,391,176 A | 2/1995 | de la Torre | |
| 5,391,182 A | 2/1995 | Chin | |
| 5,393,302 A | 2/1995 | Clark et al. | |
| RE34,871 E | 3/1995 | McGuire et al. | |
| 5,395,374 A | 3/1995 | Miller et al. | |
| 5,397,356 A | 3/1995 | Goble et al. | |
| 5,403,328 A | 4/1995 | Shallman | |
| 5,403,329 A | 4/1995 | Hinchcliffe | |
| 5,403,348 A | 4/1995 | Bonutti | |
| 5,405,359 A | 4/1995 | Pierce | |
| 5,411,550 A | 5/1995 | Herweck et al. | |
| 5,415,658 A | 5/1995 | Kilpela et al. | |
| 5,417,690 A | 5/1995 | Sennett et al. | |
| 5,417,691 A | 5/1995 | Hayhurst | |
| 5,417,698 A | 5/1995 | Green et al. | |
| 5,417,712 A | 5/1995 | Whittaker et al. | |
| 5,423,819 A | 6/1995 | Small et al. | |
| 5,423,821 A | 6/1995 | Pasque | |
| 5,423,823 A | 6/1995 | Schmieding | |
| 5,423,824 A | 6/1995 | Akerfeldt et al. | |
| 5,423,860 A | 6/1995 | Lizardi et al. | |
| 5,425,733 A | 6/1995 | Schmieding | |
| 5,425,766 A * | 6/1995 | Bowald | 623/13.18 |
| 5,433,751 A | 7/1995 | Christel et al. | |
| 5,437,680 A | 8/1995 | Yoon | |
| 5,437,685 A | 8/1995 | Blasnik | |
| 5,439,684 A | 8/1995 | Prewett et al. | |
| 5,441,508 A | 8/1995 | Gazielly et al. | |
| 5,443,468 A | 8/1995 | Johnson | |
| 5,443,482 A | 8/1995 | Stone et al. | |
| 5,443,483 A | 8/1995 | Kirsch et al. | |
| 5,443,509 A | 8/1995 | Boucher et al. | |
| 5,445,833 A | 8/1995 | Badylak et al. | |
| 5,447,512 A | 9/1995 | Wilson et al. | |
| 5,449,361 A | 9/1995 | Preissman | |
| 5,451,203 A | 9/1995 | Lamb | |
| 5,454,811 A | 10/1995 | Huebner | |
| 5,454,821 A | 10/1995 | Harm et al. | |
| 5,456,685 A | 10/1995 | Huebner | |
| 5,456,721 A * | 10/1995 | Legrand | 623/13.15 |
| 5,456,722 A | 10/1995 | McLeod et al. | |
| 5,458,601 A | 10/1995 | Young, Jr. et al. | |
| 5,458,604 A | 10/1995 | Schmieding | |
| 5,462,542 A | 10/1995 | Alesi, Jr. | |
| 5,462,560 A | 10/1995 | Stevens | |
| 5,464,426 A | 11/1995 | Bonutti | |
| 5,464,427 A | 11/1995 | Curtis et al. | |
| 5,464,440 A | 11/1995 | Johansson et al. | |
| 5,466,237 A | 11/1995 | Byrd, III et al. | |
| 5,467,786 A | 11/1995 | Allen et al. | |
| 5,470,334 A | 11/1995 | Ross et al. | |
| 5,470,337 A | 11/1995 | Moss | |
| 5,470,338 A | 11/1995 | Whitfield et al. | |
| 5,472,452 A | 12/1995 | Trott | |
| 5,474,565 A | 12/1995 | Trott | |
| 5,474,568 A | 12/1995 | Scott | |
| 5,474,572 A | 12/1995 | Hayhurst | |
| 5,476,465 A | 12/1995 | Preissman | |
| 5,478,344 A | 12/1995 | Stone et al. | |
| 5,478,345 A | 12/1995 | Stone et al. | |
| 5,480,403 A | 1/1996 | Lee et al. | |
| 5,480,406 A | 1/1996 | Nolan et al. | |
| 5,484,442 A | 1/1996 | Melker et al. | |
| 5,486,197 A | 1/1996 | Le et al. | |
| 5,486,359 A | 1/1996 | Caplan et al. | |
| 5,490,750 A | 2/1996 | Gundy | |
| 5,495,974 A | 3/1996 | Deschenes et al. | |
| 5,496,290 A | 3/1996 | Ackerman | |
| 5,496,331 A | 3/1996 | Xu et al. | |
| 5,496,348 A | 3/1996 | Bonutti | |
| 5,498,302 A | 3/1996 | Davidson | |
| 5,500,000 A | 3/1996 | Feagin et al. | |
| 5,505,735 A | 4/1996 | Li | |
| 5,505,736 A | 4/1996 | Reimels et al. | |
| 5,507,754 A | 4/1996 | Green et al. | |
| 5,520,691 A | 5/1996 | Branch | |
| 5,520,694 A | 5/1996 | Dance et al. | |
| 5,520,700 A | 5/1996 | Beyar et al. | |
| 5,520,702 A | 5/1996 | Sauer et al. | |
| 5,522,817 A | 6/1996 | Sander et al. | |
| 5,522,820 A | 6/1996 | Caspari et al. | |
| 5,522,843 A | 6/1996 | Zang | |
| 5,522,844 A | 6/1996 | Johnson | |
| 5,522,845 A | 6/1996 | Wenstrom, Jr. | |
| 5,522,846 A | 6/1996 | Bonutti | |
| 5,524,946 A | 6/1996 | Thompson | |
| 5,527,321 A | 6/1996 | Hinchliffe | |
| 5,527,342 A | 6/1996 | Pietrzak et al. | |
| 5,527,343 A | 6/1996 | Bonutti | |
| 5,531,759 A | 7/1996 | Kensey et al. | |
| 5,534,012 A | 7/1996 | Bonutti | |
| 5,534,033 A | 7/1996 | Simpson | |
| 5,536,270 A | 7/1996 | Songer et al. | |
| 5,540,698 A | 7/1996 | Preissman | |
| 5,540,703 A | 7/1996 | Barker, Jr. et al. | |
| 5,540,718 A | 7/1996 | Bartlett | |
| 5,545,168 A | 8/1996 | Burke | |
| 5,545,178 A * | 8/1996 | Kensey et al. | 606/213 |
| 5,545,180 A | 8/1996 | Le et al. | |
| 5,545,228 A | 8/1996 | Kambin | |
| 5,549,613 A | 8/1996 | Goble et al. | |
| 5,549,617 A | 8/1996 | Green et al. | |
| 5,549,619 A | 8/1996 | Peters et al. | |
| 5,549,630 A | 8/1996 | Bonutti | |
| 5,549,631 A | 8/1996 | Bonutti | |
| 5,562,664 A | 10/1996 | Durlacher et al. | |
| 5,562,668 A | 10/1996 | Johnson | |
| 5,562,669 A | 10/1996 | McGuire | |
| 5,562,683 A | 10/1996 | Chan | |

(56) References Cited

U.S. PATENT DOCUMENTS

| | | | |
|---|---|---|---|
| 5,562,685 | A | 10/1996 | Mollenauer et al. |
| 5,562,686 | A | 10/1996 | Sauer et al. |
| 5,569,269 | A | 10/1996 | Hart et al. |
| 5,569,305 | A | 10/1996 | Bonutti |
| 5,570,706 | A | 11/1996 | Howell |
| 5,571,090 | A | 11/1996 | Sherts |
| 5,571,104 | A | 11/1996 | Li |
| 5,571,139 | A | 11/1996 | Jenkins, Jr. |
| 5,572,655 | A | 11/1996 | Tuljapurkar et al. |
| 5,573,286 | A | 11/1996 | Rogozinski |
| 5,573,542 | A | 11/1996 | Stevens |
| 5,573,547 | A | 11/1996 | LeVeen et al. |
| 5,573,548 | A | 11/1996 | Nazre et al. |
| 5,577,299 | A | 11/1996 | Thompson et al. |
| 5,578,057 | A | 11/1996 | Wenstrom, Jr. |
| 5,584,695 | A | 12/1996 | Lal Sachdeva et al. |
| 5,584,835 | A | 12/1996 | Greenfield |
| 5,584,836 | A | 12/1996 | Ballintyn et al. |
| 5,584,862 | A | 12/1996 | Bonutti |
| 5,586,986 | A | 12/1996 | Hinchliffe |
| 5,588,575 | A | 12/1996 | Davignon |
| 5,591,180 | A | 1/1997 | Hinchliffe |
| 5,591,181 | A | 1/1997 | Stone et al. |
| 5,591,207 | A | 1/1997 | Coleman |
| 5,593,407 | A | 1/1997 | Reis et al. |
| 5,593,425 | A | 1/1997 | Bonutti et al. |
| 5,601,557 | A | 2/1997 | Hayhurst |
| 5,601,559 | A | 2/1997 | Melker et al. |
| 5,601,571 | A | 2/1997 | Moss |
| 5,603,716 | A | 2/1997 | Morgan et al. |
| 5,607,429 | A | 3/1997 | Hayano et al. |
| 5,607,430 | A | 3/1997 | Bailey |
| 5,613,971 | A | 3/1997 | Lower et al. |
| 5,618,290 | A | 4/1997 | Toy et al. |
| 5,626,611 | A | 5/1997 | Liu et al. |
| 5,626,614 | A | 5/1997 | Hart |
| 5,628,756 | A | 5/1997 | Barker, Jr. et al. |
| 5,628,766 | A | 5/1997 | Johnson |
| 5,630,824 | A | 5/1997 | Hart |
| 5,632,745 | A | 5/1997 | Schwartz |
| 5,632,748 | A | 5/1997 | Beck, Jr. et al. |
| 5,641,256 | A | 6/1997 | Gundy |
| 5,643,266 | A | 7/1997 | Li |
| 5,643,269 | A | 7/1997 | Harle et al. |
| 5,643,273 | A | 7/1997 | Clark |
| 5,643,295 | A | 7/1997 | Yoon |
| 5,643,319 | A | 7/1997 | Green et al. |
| 5,643,320 | A | 7/1997 | Lower et al. |
| 5,643,321 | A | 7/1997 | McDevitt |
| 5,645,546 | A | 7/1997 | Fard |
| 5,645,547 | A | 7/1997 | Coleman |
| 5,645,568 | A | 7/1997 | Chervitz et al. |
| 5,645,588 | A | 7/1997 | Graf et al. |
| 5,647,874 | A | 7/1997 | Hayhurst |
| 5,649,959 | A | 7/1997 | Hannam et al. |
| 5,649,960 | A | 7/1997 | Pavletic |
| 5,649,963 | A | 7/1997 | McDevitt |
| 5,658,289 | A | 8/1997 | Boucher et al. |
| 5,658,299 | A | 8/1997 | Hart |
| 5,658,313 | A | 8/1997 | Thal |
| 5,662,658 | A | 9/1997 | Wenstrom, Jr. |
| 5,662,663 | A | 9/1997 | Shallman |
| 5,662,677 | A | 9/1997 | Wimmer |
| 5,662,681 | A | 9/1997 | Nash et al. |
| 5,665,112 | A | 9/1997 | Thal |
| 5,667,513 | A | 9/1997 | Torrie et al. |
| 5,671,695 | A | 9/1997 | Schroeder |
| 5,674,224 | A | 10/1997 | Howell et al. |
| 5,679,723 | A | 10/1997 | Cooper et al. |
| 5,681,334 | A | 10/1997 | Evans et al. |
| 5,681,352 | A | 10/1997 | Clancy, III et al. |
| 5,683,404 | A | 11/1997 | Johnson |
| 5,683,419 | A | 11/1997 | Thal |
| 5,688,284 | A | 11/1997 | Chervitz et al. |
| 5,688,285 | A | 11/1997 | Yamada et al. |
| 5,690,655 | A | 11/1997 | Hart et al. |
| 5,690,676 | A | 11/1997 | DiPoto et al. |
| 5,690,678 | A | 11/1997 | Johnson |
| 5,693,046 | A | 12/1997 | Songer et al. |
| 5,695,497 | A | 12/1997 | Stahelin et al. |
| 5,697,929 | A | 12/1997 | Mellinger |
| 5,699,657 | A | 12/1997 | Paulson |
| 5,702,397 | A | 12/1997 | Goble et al. |
| 5,702,422 | A | 12/1997 | Stone |
| 5,702,462 | A | 12/1997 | Oberlander |
| 5,707,373 | A | 1/1998 | Sevrain et al. |
| 5,709,708 | A | 1/1998 | Thal |
| 5,711,969 | A | 1/1998 | Patel et al. |
| 5,713,005 | A | 1/1998 | Proebsting |
| 5,713,897 | A | 2/1998 | Goble et al. |
| 5,713,904 | A | 2/1998 | Errico et al. |
| 5,713,905 | A | 2/1998 | Goble et al. |
| 5,713,921 | A | 2/1998 | Bonutti |
| 5,715,578 | A | 2/1998 | Knudson |
| 5,716,359 | A | 2/1998 | Ojima et al. |
| 5,716,397 | A | 2/1998 | Myers |
| 5,716,616 | A | 2/1998 | Prockop et al. |
| 5,718,717 | A | 2/1998 | Bonutti |
| 5,720,747 | A | 2/1998 | Burke |
| 5,720,765 | A | 2/1998 | Thal |
| 5,720,766 | A | 2/1998 | Zang et al. |
| 5,722,976 | A | 3/1998 | Brown |
| 5,723,331 | A | 3/1998 | Tubo et al. |
| 5,725,529 | A | 3/1998 | Nicholson et al. |
| 5,725,549 | A | 3/1998 | Lam |
| 5,725,556 | A | 3/1998 | Moser et al. |
| 5,725,557 | A | 3/1998 | Gatturna et al. |
| 5,725,581 | A | 3/1998 | Br.ang.nemark |
| 5,725,582 | A | 3/1998 | Bevan et al. |
| 5,726,722 | A | 3/1998 | Uehara et al. |
| 5,728,107 | A | 3/1998 | Zlock et al. |
| 5,728,109 | A | 3/1998 | Schulze et al. |
| 5,728,136 | A | 3/1998 | Thal |
| 5,733,293 | A | 3/1998 | Scirica et al. |
| 5,733,306 | A | 3/1998 | Bonutti |
| 5,733,307 | A | 3/1998 | Dinsdale |
| 5,735,875 | A | 4/1998 | Bonutti et al. |
| 5,741,259 | A | 4/1998 | Chan |
| 5,741,260 | A | 4/1998 | Songer et al. |
| 5,741,281 | A | 4/1998 | Martin et al. |
| 5,743,912 | A | 4/1998 | Lahille et al. |
| 5,746,751 | A | 5/1998 | Sherts |
| 5,746,752 | A | 5/1998 | Burkhart |
| 5,746,754 | A | 5/1998 | Chan |
| 5,749,898 | A | 5/1998 | Schulze et al. |
| 5,755,729 | A | 5/1998 | de la Torre et al. |
| 5,755,791 | A | 5/1998 | Whitson et al. |
| 5,766,176 | A | 6/1998 | Duncan |
| 5,766,218 | A | 6/1998 | Arnott |
| 5,766,250 | A | 6/1998 | Chervitz et al. |
| 5,769,894 | A | 6/1998 | Ferragamo |
| 5,769,899 | A | 6/1998 | Schwartz et al. |
| 5,772,673 | A | 6/1998 | Cuny et al. |
| 5,776,196 | A | 7/1998 | Matsuzaki et al. |
| 5,776,200 | A | 7/1998 | Johnson et al. |
| 5,782,845 | A | 7/1998 | Shewchuk |
| 5,782,862 | A | 7/1998 | Bonutti |
| 5,782,864 | A | 7/1998 | Lizardi |
| 5,782,866 | A | 7/1998 | Wenstrom, Jr. |
| 5,782,925 | A | 7/1998 | Collazo et al. |
| 5,785,714 | A | 7/1998 | Morgan et al. |
| 5,786,217 | A | 7/1998 | Tubo et al. |
| 5,792,142 | A | 8/1998 | Galitzer |
| 5,792,149 | A | 8/1998 | Sherts et al. |
| 5,796,127 | A | 8/1998 | Hayafuji et al. |
| 5,797,913 | A | 8/1998 | Dambreville et al. |
| 5,797,915 | A | 8/1998 | Pierson, III et al. |
| 5,797,916 | A | 8/1998 | McDowell |
| 5,797,928 | A | 8/1998 | Kogasaka |
| 5,800,407 | A | 9/1998 | Eldor et al. |
| 5,810,824 | A | 9/1998 | Chan |
| 5,810,848 | A | 9/1998 | Hayhurst |
| 5,811,094 | A | 9/1998 | Caplan et al. |
| 5,814,056 | A | 9/1998 | Prosst et al. |

(56) References Cited

U.S. PATENT DOCUMENTS

| | | |
|---|---|---|
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,906,934 A | 5/1999 | Grande et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A * | 11/1999 | Evans et al. .................. 606/185 |
| 5,980,558 A | 11/1999 | Wiley |
| 5,980,559 A | 11/1999 | Bonutti |
| 5,989,252 A * | 11/1999 | Fumex .......................... 606/232 |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A * | 8/2000 | Eichhorn et al. ............ 623/13.14 |
| 6,113,604 A | 9/2000 | Whittaker et al. |

(56) References Cited

U.S. PATENT DOCUMENTS

| | | | |
|---|---|---|---|
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann et al. |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 * | 3/2001 | Johnson et al. ............ 623/13.15 |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 687,221 A1 | 9/2001 | Gaff et al. |
| 6,283,973 B1 | 9/2001 | Hubbard et al. |
| 6,283,996 B1 * | 9/2001 | Chervitz et al. ........... 623/13.14 |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-Green |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 * | 7/2002 | Rousseau .................. 623/23.64 |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 * | 11/2002 | Johnson et al. ............... 606/216 |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 * | 1/2003 | Fumex ......................... 606/232 |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |

(56) References Cited

U.S. PATENT DOCUMENTS

| | | |
|---|---|---|
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,592,622 B1 | 7/2003 | Ferguson |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 * | 9/2003 | Berube et al. ............ 606/151 |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,629,997 B2 | 10/2003 | Mansmann |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,169 B1 | 11/2003 | Slate et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,533 B2 | 11/2003 | O'Neil |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 * | 12/2003 | Swanstrom et al. ............ 606/153 |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 * | 3/2004 | Rousseau et al. ............ 623/23.64 |
| 6,716,190 B1 | 4/2004 | Glines et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,780 B2 | 6/2004 | Stout et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 * | 6/2004 | Rousseau ............ 623/23.64 |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,790,210 B1 | 9/2004 | Cragg et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,835,377 B2 | 12/2004 | Goldberg et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |

(56) References Cited

U.S. PATENT DOCUMENTS

| | | | |
|---|---|---|---|
| 6,939,379 B2 | 9/2005 | Sklar | |
| 6,949,102 B2 | 9/2005 | Andrews | |
| 6,951,565 B2 | 10/2005 | Keane et al. | |
| 6,960,214 B2 | 11/2005 | Burkinshaw | |
| 6,966,887 B1 | 11/2005 | Chin | |
| 6,966,916 B2 | 11/2005 | Kumar | |
| 6,969,391 B1 | 11/2005 | Gazzani | |
| 6,969,398 B2 | 11/2005 | Stevens et al. | |
| 6,972,027 B2 | 12/2005 | Fallin et al. | |
| 6,980,903 B2 | 12/2005 | Daniels et al. | |
| 6,984,237 B2 | 1/2006 | Hatch et al. | |
| 6,986,781 B2 | 1/2006 | Smith | |
| 6,989,034 B2 | 1/2006 | Hammer et al. | |
| 6,994,719 B2 | 2/2006 | Grafton | |
| 6,994,725 B1 | 2/2006 | Goble | |
| 7,001,429 B2 | 2/2006 | Ferguson | |
| 7,004,959 B2 | 2/2006 | Bonutti | |
| 7,008,451 B2 | 3/2006 | Justin et al. | |
| 7,048,754 B2 | 5/2006 | Martin et al. | |
| 7,052,499 B2 | 5/2006 | Steger et al. | |
| 7,066,942 B2 | 6/2006 | Treace | |
| 7,066,944 B2 | 6/2006 | Laufer et al. | |
| 7,081,126 B2 | 7/2006 | McDevitt et al. | |
| 7,083,638 B2 * | 8/2006 | Foerster | 606/232 |
| 7,087,064 B1 | 8/2006 | Hyde | |
| 7,097,654 B1 | 8/2006 | Freedland | |
| 7,105,010 B2 | 9/2006 | Hart et al. | |
| 7,112,221 B2 | 9/2006 | Harris | |
| 7,118,578 B2 | 10/2006 | West, Jr. et al. | |
| 7,118,583 B2 | 10/2006 | O'Quinn et al. | |
| 7,125,421 B2 | 10/2006 | Tremulis et al. | |
| 7,131,467 B2 | 11/2006 | Gao et al. | |
| 7,137,996 B2 | 11/2006 | Steiner et al. | |
| 7,141,066 B2 | 11/2006 | Steiner et al. | |
| 7,144,414 B2 | 12/2006 | Harvie et al. | |
| 7,148,209 B2 | 12/2006 | Hoemann et al. | |
| 7,153,127 B2 | 12/2006 | Struble et al. | |
| 7,153,307 B2 | 12/2006 | Scribner et al. | |
| 7,153,312 B1 | 12/2006 | Torrie et al. | |
| 7,153,327 B1 | 12/2006 | Metzger | |
| 7,160,285 B2 | 1/2007 | Sklar et al. | |
| 7,160,333 B2 | 1/2007 | Plouhar et al. | |
| 7,172,626 B1 | 2/2007 | Andrews | |
| 7,179,259 B1 | 2/2007 | Gibbs | |
| 7,201,722 B2 | 4/2007 | Krueger | |
| 7,207,993 B1 | 4/2007 | Baldwin et al. | |
| 7,255,675 B2 | 8/2007 | Gertner et al. | |
| 7,255,700 B2 | 8/2007 | Kaiser et al. | |
| 7,255,715 B2 | 8/2007 | Metzger | |
| 7,261,716 B2 | 8/2007 | Strobel et al. | |
| 7,264,634 B2 | 9/2007 | Schmieding | |
| 7,279,008 B2 | 10/2007 | Brown et al. | |
| 7,285,124 B2 | 10/2007 | Foerster | |
| 7,291,177 B2 | 11/2007 | Gibbs | |
| 7,303,577 B1 | 12/2007 | Dean | |
| 7,306,417 B2 | 12/2007 | Dorstewitz | |
| 7,309,355 B2 | 12/2007 | Donnelly et al. | |
| 7,326,222 B2 | 2/2008 | Dreyfuss et al. | |
| 7,329,272 B2 | 2/2008 | Burkhart et al. | |
| 7,361,179 B2 | 4/2008 | Rousseau et al. | |
| 7,377,845 B2 | 5/2008 | Stewart et al. | |
| 7,390,329 B2 | 6/2008 | Westra et al. | |
| 7,390,332 B2 | 6/2008 | Selvitelli et al. | |
| 7,399,018 B1 | 7/2008 | Khachaturian | |
| 7,442,210 B2 | 10/2008 | Segal et al. | |
| 7,465,308 B2 | 12/2008 | Sikora et al. | |
| 7,468,074 B2 | 12/2008 | Caborn et al. | |
| 7,481,814 B1 | 1/2009 | Metzger | |
| 7,485,149 B1 | 2/2009 | White | |
| 7,494,506 B2 | 2/2009 | Brulez et al. | |
| D587,807 S | 3/2009 | Wolf et al. | |
| 7,500,983 B1 | 3/2009 | Kaiser et al. | |
| 7,513,910 B2 | 4/2009 | Buskirk et al. | |
| 7,572,275 B2 | 8/2009 | Fallin et al. | |
| 7,572,298 B2 | 8/2009 | Roller et al. | |
| 7,578,825 B2 | 8/2009 | Huebner | |
| 7,585,311 B2 | 9/2009 | Green et al. | |
| 7,591,823 B2 | 9/2009 | Tipirneni | |
| 7,597,705 B2 | 10/2009 | Forsberg et al. | |
| 7,601,165 B2 | 10/2009 | Stone | |
| 7,604,636 B1 | 10/2009 | Walters et al. | |
| 7,608,092 B1 | 10/2009 | Schaffhausen | |
| 7,608,098 B1 | 10/2009 | Stone et al. | |
| 7,615,076 B2 | 11/2009 | Cauthen, III et al. | |
| 7,621,937 B2 | 11/2009 | Pipenhagen et al. | |
| 7,632,287 B2 | 12/2009 | Baker et al. | |
| 7,651,509 B2 | 1/2010 | Bojarski et al. | |
| 7,658,750 B2 | 2/2010 | Li | |
| 7,658,751 B2 | 2/2010 | Stone et al. | |
| 7,670,279 B2 | 3/2010 | Gertner | |
| 7,678,123 B2 | 3/2010 | Chanduszko | |
| 7,691,112 B2 | 4/2010 | Chanduszko et al. | |
| 7,695,493 B2 | 4/2010 | Saadat et al. | |
| 7,695,503 B1 | 4/2010 | Kaiser et al. | |
| 7,703,372 B1 | 4/2010 | Shakespeare | |
| 7,717,929 B2 | 5/2010 | Fallman | |
| 7,731,732 B2 | 6/2010 | Ken | |
| 7,736,364 B2 | 6/2010 | Stone | |
| 7,736,379 B2 | 6/2010 | Ewers et al. | |
| 7,749,250 B2 | 7/2010 | Stone et al. | |
| 7,758,594 B2 | 7/2010 | Lamson et al. | |
| 7,758,611 B2 | 7/2010 | Kato | |
| 7,762,942 B2 | 7/2010 | Neisz et al. | |
| 7,771,482 B1 | 8/2010 | Karmon | |
| 7,776,041 B1 | 8/2010 | Walters | |
| 7,790,945 B1 | 9/2010 | Watson, Jr. | |
| 7,803,173 B2 | 9/2010 | Burkhart et al. | |
| 7,819,895 B2 | 10/2010 | Ginn et al. | |
| 7,828,820 B2 | 11/2010 | Stone et al. | |
| 7,828,850 B2 | 11/2010 | Cauthen, III et al. | |
| 7,856,698 B2 | 12/2010 | Hays | |
| 7,857,830 B2 | 12/2010 | Stone et al. | |
| 7,867,252 B2 | 1/2011 | Criscuolo et al. | |
| 7,867,264 B2 | 1/2011 | McDevitt et al. | |
| 7,875,058 B2 | 1/2011 | Holmes, Jr. | |
| 7,878,058 B2 | 2/2011 | Blendinger et al. | |
| 7,887,586 B2 | 2/2011 | Linares | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,914,539 B2 | 3/2011 | Stone et al. | |
| 7,938,847 B2 | 5/2011 | Fanton et al. | |
| 7,959,650 B2 | 6/2011 | Kaiser et al. | |
| 7,981,140 B2 | 7/2011 | Burkhart | |
| 7,998,203 B2 | 8/2011 | Blum | |
| 8,034,090 B2 | 10/2011 | Stone et al. | |
| 8,062,334 B2 | 11/2011 | Green et al. | |
| 8,075,574 B2 | 12/2011 | May et al. | |
| 8,088,108 B2 | 1/2012 | Kraft | |
| 8,088,130 B2 | 1/2012 | Kaiser et al. | |
| 8,114,127 B2 | 2/2012 | West, Jr. | |
| 8,114,128 B2 | 2/2012 | Cauldwell et al. | |
| 8,118,835 B2 | 2/2012 | Weisel et al. | |
| 8,118,836 B2 | 2/2012 | Denham et al. | |
| 8,118,868 B2 | 2/2012 | May et al. | |
| 8,128,658 B2 | 3/2012 | Kaiser et al. | |
| 8,137,354 B2 | 3/2012 | Stone | |
| 8,137,382 B2 | 3/2012 | Denham et al. | |
| 8,162,997 B2 | 4/2012 | Struhl | |
| 8,167,906 B2 | 5/2012 | Cauldwell et al. | |
| 8,177,810 B2 | 5/2012 | Ferree | |
| 8,202,318 B2 | 6/2012 | Willobee | |
| 8,221,454 B2 | 7/2012 | Schaffhausen | |
| 8,231,654 B2 | 7/2012 | Kaiser et al. | |
| 8,251,998 B2 | 8/2012 | Hoeppner et al. | |
| 8,252,022 B2 | 8/2012 | Holman et al. | |
| 8,273,106 B2 | 9/2012 | Stone et al. | |
| 8,292,921 B2 | 10/2012 | Stone et al. | |
| 8,298,262 B2 | 10/2012 | Stone et al. | |
| 8,298,284 B2 | 10/2012 | Cassani | |
| 8,303,604 B2 | 11/2012 | Stone et al. | |
| 8,317,825 B2 | 11/2012 | Stone | |
| 8,337,525 B2 | 12/2012 | Stone et al. | |
| 8,343,155 B2 | 1/2013 | Fisher et al. | |

(56) References Cited

U.S. PATENT DOCUMENTS

| | | | |
|---|---|---|---|
| 8,343,227 B2 | 1/2013 | Metzger et al. | |
| 8,361,054 B2 | 1/2013 | Ducharme et al. | |
| 8,361,113 B2 | 1/2013 | Stone et al. | |
| 8,409,253 B2 | 4/2013 | Stone et al. | |
| 8,486,114 B2 | 7/2013 | Gillard et al. | |
| 8,500,818 B2 | 8/2013 | Metzger et al. | |
| 8,506,597 B2 | 8/2013 | Kaiser et al. | |
| 8,551,140 B2 | 10/2013 | Denham et al. | |
| 8,562,645 B2 | 10/2013 | Stone et al. | |
| 8,562,647 B2 | 10/2013 | Kaiser et al. | |
| 8,574,235 B2 | 11/2013 | Stone | |
| 8,579,944 B2 | 11/2013 | Holloway et al. | |
| 8,597,327 B2 | 12/2013 | Stone et al. | |
| 8,608,777 B2 | 12/2013 | Kaiser et al. | |
| 8,632,566 B2 | 1/2014 | Olson | |
| 8,632,569 B2 | 1/2014 | Stone et al. | |
| 8,652,171 B2 | 2/2014 | Stone et al. | |
| 8,652,172 B2 | 2/2014 | Denham et al. | |
| 8,672,904 B1 | 3/2014 | Schultz | |
| 8,672,968 B2 | 3/2014 | Stone et al. | |
| 8,672,969 B2 | 3/2014 | Stone et al. | |
| 8,721,650 B2 | 5/2014 | Fanton et al. | |
| 8,721,684 B2 | 5/2014 | Denham et al. | |
| 8,771,316 B2 | 7/2014 | Denham et al. | |
| 8,771,352 B2 | 7/2014 | Conner et al. | |
| 8,777,956 B2 | 7/2014 | Hoeppner et al. | |
| 8,801,783 B2 | 8/2014 | Stone et al. | |
| 8,840,645 B2 | 9/2014 | Denham et al. | |
| 8,900,314 B2 | 12/2014 | Metzger et al. | |
| 8,926,613 B2 | 1/2015 | Kaiser et al. | |
| 8,932,331 B2 | 1/2015 | Kaiser et al. | |
| 8,936,621 B2 | 1/2015 | Denham et al. | |
| 8,968,364 B2 | 3/2015 | Berelsman et al. | |
| 8,998,949 B2 | 4/2015 | Stone et al. | |
| 9,005,287 B2 | 4/2015 | Stone | |
| 9,017,381 B2 | 4/2015 | Kaiser et al. | |
| 9,023,058 B2 | 5/2015 | Jaramillo et al. | |
| 9,078,644 B2 | 7/2015 | Stone | |
| 9,149,267 B2 | 10/2015 | Norton et al. | |
| 9,173,651 B2 | 11/2015 | Stone et al. | |
| 9,198,673 B2 | 12/2015 | Stone | |
| 9,216,078 B2 | 12/2015 | Conner et al. | |
| 9,271,713 B2 | 3/2016 | Denham et al. | |
| 2001/0010005 A1 | 7/2001 | Kammerer et al. | |
| 2001/0014825 A1 | 8/2001 | Burke et al. | |
| 2001/0019649 A1 | 9/2001 | Field et al. | |
| 2001/0029387 A1 | 10/2001 | Wolf et al. | |
| 2001/0037131 A1 | 11/2001 | Schmieding et al. | |
| 2001/0037153 A1 | 11/2001 | Rockwood et al. | |
| 2001/0041916 A1 | 11/2001 | Bonutti | |
| 2001/0041937 A1 | 11/2001 | Rieser et al. | |
| 2001/0041938 A1* | 11/2001 | Hein | 623/13.13 |
| 2001/0044639 A1 | 11/2001 | Levinson | |
| 2001/0047206 A1 | 11/2001 | Sklar et al. | |
| 2001/0051815 A1 | 12/2001 | Esplin | |
| 2001/0051816 A1 | 12/2001 | Enzerink et al. | |
| 2001/0053934 A1 | 12/2001 | Schmieding | |
| 2002/0001964 A1 | 1/2002 | Choi | |
| 2002/0004669 A1 | 1/2002 | Bartlett | |
| 2002/0007182 A1 | 1/2002 | Kim | |
| 2002/0010513 A1 | 1/2002 | Schmieding | |
| 2002/0013607 A1 | 1/2002 | Lemer | |
| 2002/0013608 A1 | 1/2002 | ElAttrache et al. | |
| 2002/0019649 A1 | 2/2002 | Sikora et al. | |
| 2002/0029066 A1 | 3/2002 | Foerster | |
| 2002/0032465 A1 | 3/2002 | Lemer | |
| 2002/0055780 A1 | 5/2002 | Sklar | |
| 2002/0058966 A1 | 5/2002 | Tormala et al. | |
| 2002/0068254 A1 | 6/2002 | Campbell | |
| 2002/0077629 A1 | 6/2002 | Hoffman et al. | |
| 2002/0077659 A1 | 6/2002 | Johnson et al. | |
| 2002/0082220 A1 | 6/2002 | Hoemann et al. | |
| 2002/0099411 A1 | 7/2002 | Bartlett | |
| 2002/0111591 A1 | 8/2002 | Mckinnon et al. | |
| 2002/0111653 A1 | 8/2002 | Foerster | |
| 2002/0120270 A1 | 8/2002 | Trieu et al. | |
| 2002/0120292 A1 | 8/2002 | Morgan | |
| 2002/0123752 A1 | 9/2002 | Schultheiss et al. | |
| 2002/0128654 A1 | 9/2002 | Steger et al. | |
| 2002/0128684 A1* | 9/2002 | Foerster | 606/232 |
| 2002/0129820 A1 | 9/2002 | Ryan et al. | |
| 2002/0143336 A1 | 10/2002 | Hearn | |
| 2002/0147463 A1 | 10/2002 | Martinek | |
| 2002/0156475 A1 | 10/2002 | Lerch et al. | |
| 2002/0161401 A1 | 10/2002 | Steiner | |
| 2002/0161439 A1* | 10/2002 | Strobel et al. | 623/13.14 |
| 2002/0165548 A1 | 11/2002 | Jutley | |
| 2002/0165611 A1 | 11/2002 | Enzerink et al. | |
| 2002/0169452 A1 | 11/2002 | Tormala et al. | |
| 2002/0169477 A1 | 11/2002 | Demopulos et al. | |
| 2002/0169478 A1 | 11/2002 | Schwartz et al. | |
| 2002/0173788 A1 | 11/2002 | Bojarski et al. | |
| 2002/0177853 A1 | 11/2002 | Chervitz et al. | |
| 2002/0188298 A1 | 12/2002 | Chan | |
| 2002/0193830 A1 | 12/2002 | Bonutti | |
| 2003/0004545 A1 | 1/2003 | Burkhart et al. | |
| 2003/0009235 A1 | 1/2003 | Manrique et al. | |
| 2003/0023268 A1 | 1/2003 | Lizardi | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0065391 A1 | 4/2003 | Re et al. | |
| 2003/0065402 A1 | 4/2003 | Anderson et al. | |
| 2003/0078585 A1 | 4/2003 | Johnson et al. | |
| 2003/0078603 A1 | 4/2003 | Schaller et al. | |
| 2003/0078617 A1 | 4/2003 | Schwartz et al. | |
| 2003/0083662 A1 | 5/2003 | Middleton | |
| 2003/0083694 A1 | 5/2003 | Miller | |
| 2003/0088251 A1 | 5/2003 | Braun et al. | |
| 2003/0088272 A1 | 5/2003 | Smith | |
| 2003/0105477 A1 | 6/2003 | Schwartz et al. | |
| 2003/0105489 A1 | 6/2003 | Eichhorn et al. | |
| 2003/0120309 A1 | 6/2003 | Colleran et al. | |
| 2003/0130670 A1 | 7/2003 | Anderson et al. | |
| 2003/0130694 A1 | 7/2003 | Bojarski et al. | |
| 2003/0130695 A1 | 7/2003 | McDevitt et al. | |
| 2003/0135214 A1 | 7/2003 | Fetto et al. | |
| 2003/0135239 A1 | 7/2003 | Gabriel et al. | |
| 2003/0135963 A1 | 7/2003 | Holbrook et al. | |
| 2003/0139752 A1 | 7/2003 | Pasricha et al. | |
| 2003/0139775 A1 | 7/2003 | Grafton | |
| 2003/0149448 A1 | 8/2003 | Foerster et al. | |
| 2003/0152522 A1 | 8/2003 | Miller et al. | |
| 2003/0153947 A1 | 8/2003 | Koseki | |
| 2003/0167072 A1 | 9/2003 | Oberlander | |
| 2003/0167090 A1 | 9/2003 | Chervitz et al. | |
| 2003/0171811 A1 | 9/2003 | Steiner et al. | |
| 2003/0176865 A1 | 9/2003 | Supinski | |
| 2003/0176919 A1 | 9/2003 | Schmieding | |
| 2003/0176920 A1 | 9/2003 | Sklar et al. | |
| 2003/0181925 A1 | 9/2003 | Bain et al. | |
| 2003/0195528 A1 | 10/2003 | Ritchart | |
| 2003/0195564 A1* | 10/2003 | Tran et al. | 606/232 |
| 2003/0208209 A1 | 11/2003 | Gambale et al. | |
| 2003/0208210 A1 | 11/2003 | Dreyfuss et al. | |
| 2003/0212456 A1 | 11/2003 | Lipchitz et al. | |
| 2003/0216809 A1 | 11/2003 | Ferguson | |
| 2003/0220646 A1 | 11/2003 | Thelen et al. | |
| 2003/0220660 A1 | 11/2003 | Kortenbach et al. | |
| 2003/0225459 A1 | 12/2003 | Hammer et al. | |
| 2003/0229361 A1 | 12/2003 | Jackson | |
| 2003/0229396 A1 | 12/2003 | Andrews | |
| 2003/0236555 A1* | 12/2003 | Thornes | 606/232 |
| 2004/0002734 A1* | 1/2004 | Fallin et al. | 606/232 |
| 2004/0006345 A1 | 1/2004 | Vlahos et al. | |
| 2004/0006346 A1 | 1/2004 | Holmen et al. | |
| 2004/0015171 A1 | 1/2004 | Bojarski et al. | |
| 2004/0015172 A1 | 1/2004 | Biedermann et al. | |
| 2004/0024456 A1 | 2/2004 | Brown et al. | |
| 2004/0024457 A1 | 2/2004 | Boyce et al. | |
| 2004/0039389 A1 | 2/2004 | West et al. | |
| 2004/0044391 A1 | 3/2004 | Porter | |

(56) References Cited

U.S. PATENT DOCUMENTS

| | | |
|---|---|---|
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033363 A1* | 2/2005 | Bojarski et al. ............... 606/228 |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1* | 6/2005 | Pipenhagen et al. .......... 606/213 |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1* | 11/2005 | Saadat et al. ................. 606/232 |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1* | 12/2005 | Stone et al. ................... 606/151 |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |

(56) References Cited

U.S. PATENT DOCUMENTS

| | | |
|---|---|---|
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178743 A1 | 8/2006 | Carter |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1 | 11/2006 | Burkhart et al. |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 * | 12/2006 | Bojarski et al. ............... 606/232 |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147187 A1 | 6/2008 | Bollinger et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0281428 A1 | 11/2008 | Meyers et al. |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |

(56) References Cited

U.S. PATENT DOCUMENTS

| | | |
|---|---|---|
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087225 A1 | 4/2011 | Fritzinger |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsnnan et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |

(56) References Cited

U.S. PATENT DOCUMENTS

| | | |
|---|---|---|
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |
| 2016/0081789 A1 | 3/2016 | Denham et al. |

FOREIGN PATENT DOCUMENTS

| | | |
|---|---|---|
| AU | 4381268 A | 4/1970 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 1713188 A | 11/1989 |
| AU | 651929 | 8/1994 |
| CN | 105208970 A | 12/2015 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 29922088 U1 | 4/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0447065 A2 | 9/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 1741412 A2 | 1/2007 |
| EP | 1864617 A2 | 12/2007 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2634373 A1 | 1/1990 |
| FR | 2655840 | 6/1991 |
| FR | 2663837 A1 | 1/1992 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2734709 A1 | 12/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2129306 A | 5/1984 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 54166092 U | 11/1979 |
| JP | 54166093 U | 11/1979 |
| JP | 54176284 U | 12/1979 |
| JP | 54178988 U | 12/1979 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10127672 A | 5/1998 |
| JP | 10211213 | 8/1998 |
| RU | 2051647 C1 | 1/1996 |
| RU | 2076667 C1 | 4/1997 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |

(56) References Cited

FOREIGN PATENT DOCUMENTS

| WO | WO-9737603 | 10/1997 |
|---|---|---|
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 A1 | 12/2005 |
| WO | WO-2006023661 A2 | 3/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.
International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.
US 6,238,418, 5/2001, Schwartz et al. (withdrawn).
"AperFix® System Surgical Technique Guide. Single Tunnel Double Bundle.™ " Cayenne Medical brochure. (Aug. 2008) 8 sheets.
"Arthroscopic Meniscal Repair using the Meniscal Cinch™ ", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex® , Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare lnterferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/02634 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.

(56) References Cited

OTHER PUBLICATIONS

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
International Search Report and Written Opinion mailed Mar. 6, 2014 for PCT/US2013/075989 which claims benefit of U.S. Appl. No. 13/720,648, filed Dec. 19, 2012.
U.S. Appl. No. 10/984,624, Final Office Action mailed Jan. 5, 2009, 9 pgs.
U.S. Appl. No. 10/984,624, Non Final Office Action mailed Jun. 12, 2009, 9 pgs.
U.S. Appl. No. 10/984,624, Notice of Allowance mailed Jun. 12, 2009, 9 pgs.
U.S. Appl. No. 10/984,624, Response filed Apr. 1, 2009 to Final Office Action mailed Jan. 5, 2009, 16 pgs.
U.S. Appl. No. 10/984,624, Response filed Apr. 15, 2008 to Restriction Requirement mailed Mar. 24, 2008, 1 pg.
U.S. Appl. No. 10/984,624, Response filed Oct. 10, 2008 to Non Final Office Action mailed Jun. 12, 2009, 12 pgs.
U.S. Appl. No. 10/984,624, Restriction Requirement mailed Mar. 24, 2008, 5 pgs.
U.S. Appl. No. 11/294,694, Final Office Action mailed Sep. 1, 2010, 14 pgs.
U.S. Appl. No. 11/294,694, Non Final Office Action mailed Mar. 16 2010, 19 pgs.
U.S. Appl. No. 11/294,694, Notice of Allowance mailed Nov. 17, 2010, 4 pgs.
U.S. Appl. No. 11/294,694, Preliminary Amendment filed Jan. 13, 2010, 9 pgs.
U.S. Appl. No. 11/294,694, Response filed Jun. 16, 2010 to Non Final Office Action mailed Mar. 16, 2010, 16 pgs.
U.S. Appl. No. 11/294,694, Response filed Nov. 1, 2010 to Final Office Action mailed Sep. 1, 2010, 10 pgs.
U.S. Appl. No. 11/294,694, Response filed Nov. 22, 2009 to Restriction Requirement mailed Nov. 25, 2009, 1 pg.
U.S. Appl. No. 11/294,694, Restriction Requirement mailed Nov. 25, 2009, 9 pgs.
U.S. Appl. No. 11/347,661, Examiner Interview Summary mailed Sep. 11, 2009, 2 pgs.
U.S. Appl. No. 11/347,661, Final Office Action mailed Mar. 3, 2009, 15 pgs.
U.S. Appl. No. 11/347,661, Non Final Office Action mailed Aug. 13, 2009, 19 pgs.
U.S. Appl. No. 11/347,661, Non Final Office Action mailed Aug. 21, 2008, 11 pgs.
U.S. Appl. No. 11/347,661, Notice of Allowance mailed Feb. 24, 2010, 8 pgs.
U.S. Appl. No. 11/347,661, Notice of Allowance mailed May 5, 2010, 8 pgs.
U.S. Appl. No. 11/347,661, Response filed May. 29, 2008 to Restriction Requirement mailed Apr. 30, 2008, 1 pg.
U.S. Appl. No. 11/347,661, Response filed Jun. 3, 2009 to Final Office Action mailed Mar. 3, 2009, 19 pgs.
U.S. Appl. No. 11/347,661, Response filed Nov. 6, 2009 to Non Final Office Action mailed Aug. 13, 2009, 16 pgs.
U.S. Appl. No. 11/347,661, Response filed Nov. 19, 2008 to Non Final Office Action mailed Aug. 21, 2008, 12 pgs.
U.S. Appl. No. 11/347,661, Restriction Requirement mailed Apr. 30, 2008, 6 pgs.
U.S. Appl. No. 11/347,662, Examiner Interview Summary mailed Jun. 24, 2010, 3 pgs.
U.S. Appl. No. 11/347,662, Examiner Interview Summary mailed Nov. 9, 2009, 3 pgs.
U.S. Appl. No. 11/347,662, Final Office Action mailed Sep. 16, 2009, 13 pgs.
U.S. Appl. No. 11/347,662, Final Office Action mailed Oct. 26, 2010, 10 pgs.
U.S. Appl. No. 11/347,662, Non Final Office Action mailed Mar. 9, 2009, 11 pgs.
U.S. Appl. No. 11/347,662, Non Final Office Action mailed May 21, 2010, 19 pgs.
U.S. Appl. No. 11/347,662, Non Final Office Action mailed Oct. 28, 2008, 13 pgs.
U.S. Appl. No. 11/347,662, Response filed Jan. 16, 2009 to Non Final Office Action mailed Oct. 28, 2008, 16 pgs.
U.S. Appl. No. 11/347,662, Response filed Feb. 12, 2010 to Final Office Action mailed Sep. 16, 2009, 21 pgs.
U.S. Appl. No. 11/347,662, Response filed Jun. 5, 2009 to Non Final Office Action mailed Mar. 9, 2009, 13 pgs.
U.S. Appl. No. 11/347,662, Response filed Aug. 20, 2010 to Non Final Office Action mailed May 21, 2010, 13 pgs.
U.S. Appl. No. 11/386,071, Advisory Action mailed Dec. 23, 2010, 3 pgs.
U.S. Appl. No. 11/386,071, Examiner Interview Summary mailed Jan. 31, 2011, 3 pgs.
U.S. Appl. No. 11/386,071, Examiner Interview Summary mailed Jul. 21, 2010, 3 pgs.
U.S. Appl. No. 11/386,071, Final Office Action mailed Oct. 27, 2010, 10 pgs.
U.S. Appl. No. 11/386,071, Non Final Office Action mailed May 12, 2010, 13 pgs.
U.S. Appl. No. 11/386,071, Notice of Allowance mailed Jun. 6, 2011, 6 pgs.
U.S. Appl. No. 11/386,071, Response filed Jan. 26, 2011 to Advisory Action mailed Dec. 23, 2010, 13 pgs.
U.S. Appl. No. 11/386,071, Response filed Aug. 12, 2010 to Non Final Office Action mailed May 12, 2010, 14 pgs.
U.S. Appl. No. 11/386,071, Response filed Dec. 15, 2010 to Final Office Action mailed Oct. 27, 2010, 14 pgs.
U.S. Appl. No. 11/408,282, Final Office Action mailed Dec. 15, 2008, 8 pgs.
U.S. Appl. No. 11/408,282, Non Final Office Action mailed May 23, 2008, 12 pgs.
U.S. Appl. No. 11/408,282, Response filed Aug. 21, 2008 to Non Final Office Action mailed May 23, 2008, 10 pgs.
U.S. Appl. No. 11/504,882, Examiner Interview Summary mailed Sep. 2, 2010, 3 pgs.
U.S. Appl. No. 11/504,882, Final Office Action mailed Dec. 21, 2010, 7 pgs.

(56) References Cited

OTHER PUBLICATIONS

U.S. Appl. No. 11/504,882, Non Final Office Action mailed Jun. 19, 2014, 11 pgs.
U.S. Appl. No. 11/504,882, Non Final Office Action mailed Jun. 23, 2010, 8 pgs.
U.S. Appl. No. 11/504,882, Non Final Office Action mailed Nov. 13, 2013, 13 pgs.
U.S. Appl. No. 11/504,882, Notice of Allowance mailed Dec. 1, 2014, 9 pgs.
U.S. Appl. No. 11/504,882, Response filed Feb. 10, 2014 to Non Final Office Action mailed Nov. 13, 2013, 11 pgs.
U.S. Appl. No. 11/504,882, Response filed Mar. 18, 2011 to Final Office Action mailed Dec. 21, 2010, 11 pgs.
U.S. Appl. No. 11/504,882, Response filed Sep. 17, 2014 to Non Final Office Action mailed Jun. 19, 2014, 14 pgs.
U.S. Appl. No. 11/504,882, Response filed Sep. 23, 2010 to Non Final Office Action mailed Jun. 23, 2010, 12 pgs.
U.S. Appl. No. 11/504,882, Supplemental Notice of Allowability mailed Mar. 12, 2015, 5 pgs.
U.S. Appl. No. 11/541,505, Non Final Office Action mailed May 19, 2009, 7 pgs.
U.S. Appl. No. 11/541,505, Notice of Allowance mailed Sep. 18, 2009, 8 pgs.
U.S. Appl. No. 11/541,505, Response filed Apr. 9, 2009 to Restriction Requirement mailed Mar. 9, 2009, 1 pg.
U.S. Appl. No. 11/541,505, Response filed Jun. 18, 2009 to Non Final Office Action mailed May 19, 2009, 5 pgs.
U.S. Appl. No. 11/541,505, Restriction Requirement mailed Mar. 9, 2009, 9 pgs.
U.S. Appl. No. 11/541,506, Notice of Allowance mailed Jun. 1, 2009, 10 pgs.
U.S. Appl. No. 11/541,506, Notice of Allowance mailed Jun. 29, 2009, 8 pgs.
U.S. Appl. No. 11/541,506, Response filed Apr. 9, 2009 to Restriction Requirement mailed Mar. 9, 2009, 1 pg.
U.S. Appl. No. 11/541,506, Restriction Requirement mailed Mar. 9, 2009, 6 pgs.
U.S. Appl. No. 11/739,768, Examiner Interview Summary mailed May 11, 2011, 3 pgs.
U.S. Appl. No. 11/739,768, Examiner Interview Summary mailed Oct. 4, 2011, 3 pgs.
U.S. Appl. No. 11/739,768, Final Office Action mailed Aug. 22, 2011, 14 pgs.
U.S. Appl. No. 11/739,768, Non Final Office Action mailed Mar. 4, 2011, 11 pgs.
U.S. Appl. No. 11/739,768, Notice of Allowance mailed Nov. 15, 2011, 5 pgs.
U.S. Appl. No. 11/739,768, Response filed Jun. 6, 2011 to Non Final Office Action mailed Mar. 4, 2011, 15 pgs.
U.S. Appl. No. 11/739,768, Response filed Oct. 26, 2011 to Final Office Action mailed Aug. 22, 2011, 14 pgs.
U.S. Appl. No. 11/740,035, Final Office Action mailed Aug. 7, 2008, 9 pgs.
U.S. Appl. No. 11/740,035, Non Final Office Action mailed Mar. 3, 2008, 9 pgs.
U.S. Appl. No. 11/740,035, Response filed Apr. 3, 2008 to Non Final Office Action mailed Jan. 3, 2008, 6 pgs.
U.S. Appl. No. 11/784,821, Corrected Notice of Allowance mailed Dec. 24, 2014, 4 pgs.
U.S. Appl. No. 11/784,821, Examiner Interview Summary mailed Jun. 26, 2014, 3 pgs.
U.S. Appl. No. 11/784,821, Examiner Interview Summary mailed Nov. 17, 2009, 3 pgs.
U.S. Appl. No. 11/784,821, Final Office Action mailed Mar. 10, 2010, 11 pgs.
U.S. Appl. No. 11/784,821, Non Final Office Action mailed Mar. 28, 2014, 14 pgs.
U.S. Appl. No. 11/784,821, Non Final Office Action mailed Sep. 4, 2009, 12 pgs.
U.S. Appl. No. 11/784,821, Notice of Allowance mailed Oct. 21, 2014, 10 pgs.
U.S. Appl. No. 11/784,821, Response filed Jun. 10, 2010 to Final Office Action mailed Mar. 10, 2010, 20 pgs.
U.S. Appl. No. 11/784,821, Response filed Jun. 15, 2009 to Restriction Requirement mailed May 13, 2009, 2 pgs.
U.S. Appl. No. 11/784,821, Response filed Jun. 26, 2014 to Non Final Office Action mailed Mar. 28, 2014, 16 pgs.
U.S. Appl. No. 11/784,821, Response filed Nov. 23, 2009 to Non Final Office Action mailed Sep. 4, 2009, 17 pgs.
U.S. Appl. No. 11/784,821, Restriction Requirement mailed May 13, 2009, 6 pgs.
U.S. Appl. No. 11/869,440, Examiner Interview Summary mailed Mar. 25, 2010, 3 pgs.
U.S. Appl. No. 11/869,440, Non Final Office Action mailed Mar. 1, 2010, 13 pgs.
U.S. Appl. No. 11/869,440, Notice of Allowance mailed Aug. 19, 2010, 10 pgs.
U.S. Appl. No. 11/869,440, Response filed Jun. 1, 2010 to Non Final Office Action mailed Mar. 1, 2010, 14 pgs.
U.S. Appl. No. 11/935,681, Examiner Interview Summary mailed Jul. 19, 2010, 3 pgs.
U.S. Appl. No. 11/935,681, Non Final Office Action mailed May 24, 2010, 12 pgs.
U.S. Appl. No. 11/935,681, Notice of Allowance mailed Nov. 8, 2010, 10 pgs.
U.S. Appl. No. 11/935,681, Response filed Apr. 19, 2010 to Restriction Requirement mailed Mar. 17, 2010, 4 pgs.
U.S. Appl. No. 11/935,681, Response filed Aug. 24, 2010 to Non Final Office Action mailed May 24, 2010, 13 pgs.
U.S. Appl. No. 11/935,681, Restriction Requirement mailed Mar. 17, 2010, 6 pgs.
U.S. Appl. No. 12/014,340, Examiner Interview Summary mailed Jun. 22, 2010, 3 pgs.
U.S. Appl. No. 12/014,340, Non Final Office Action mailed May 25, 2010, 12 pgs.
U.S. Appl. No. 12/014,340, Notice of Allowance mailed Nov. 8, 2010, 9 pgs.
U.S. Appl. No. 12/014,340, Preliminary Amendment filed May 21, 2010, 11 pgs.
U.S. Appl. No. 12/014,340, Response filed Apr. 26, 2010 to Restriction Requirement mailed Mar. 25, 2010, 2 pgs.
U.S. Appl. No. 12/014,340, Response filed Aug. 25, 2010 to Non Final Office Action mailed May 25, 2010, 16 pgs.
U.S. Appl. No. 12/014,340, Restriction Requirement mailed Mar. 25, 2010, 9 pgs.
U.S. Appl. No. 12/014,399, Examiner Interview Summary mailed Jun. 23, 2010, 3 pgs.
U.S. Appl. No. 12/014,399, Non Final Office Action mailed May 26, 2010, 13 pgs.
U.S. Appl. No. 12/014,399, Notice of Allowance mailed Nov. 12, 2010, 11 pgs.
U.S. Appl. No. 12/014,399, Preliminary Amendment filed May 25, 2010, 10 pgs.
U.S. Appl. No. 12/014,399, Response filed May 5, 2010 to Restriction Requirement mailed Apr. 6, 2010, 2 pgs.
U.S. Appl. No. 12/014,399, Response filed Aug. 25, 2010 to Non Final Office Action mailed May 26, 2010, 14 pgs.
U.S. Appl. No. 12/014,399, Restriction Requirement mailed Apr. 6, 2010, 9 pgs.
U.S. Appl. No. 12/029,861, Examiner Interview Summary mailed Jan. 27, 2012, 3 pgs.
U.S. Appl. No. 12/029,861, Final Office Action mailed Dec. 8, 2011, 11 pgs.
U.S. Appl. No. 12/029,861, Non Final Office Action mailed Jul. 26, 2011, 11 pgs.
U.S. Appl. No. 12/029,861, Notice of Allowance mailed Apr. 26, 2012, 5 pgs.
U.S. Appl. No. 12/029,861, Response filed Jan. 26, 2012 to Final Office Action mailed Dec. 8, 2011, 15 pgs.
U.S. Appl. No. 12/029,861, Response filed May 6, 2011 to Restriction Requirement mailed Apr. 7, 2011, 10 pgs.

(56) References Cited

OTHER PUBLICATIONS

U.S. Appl. No. 12/029,861, Response filed Jun. 23, 2011 to Restriction Requirement mailed May 24, 2011, 1 pgs.
U.S. Appl. No. 12/029,861, Response filed Oct. 14, 2011 to Non Final Office Action mailed Jul. 26, 2011, 11 pgs.
U.S. Appl. No. 12/029,861, Restriction Requirement mailed Apr. 7, 2011, 8 pgs.
U.S. Appl. No. 12/029,861, Restriction Requirement mailed May 24, 2011, 6 pgs.
U.S. Appl. No. 12/107,437, Examiner Interview Summary mailed May 10, 2010, 4 pgs.
U.S. Appl. No. 12/107,437, Non Final Office Action mailed Mar. 17, 2010, 9 pgs.
U.S. Appl. No. 12/107,437, Preliminary Amendment filed Feb. 23, 2010, 9 pgs.
U.S. Appl. No. 12/107,437, Response filed Jan. 29, 2010 to Restriction Requirement mailed Jan. 13, 2010, 1 pgs.
U.S. Appl. No. 12/107,437, Restriction Requirement mailed Jan. 13, 2010, 7 pgs.
U.S. Appl. No. 12/196,398, Examiner Interview Summary mailed Nov. 8, 2010, 3 pgs.
U.S. Appl. No. 12/196,398, Notice of Allowance mailed Feb. 3, 2011, 12 pgs.
U.S. Appl. No. 12/196,398, Preliminary Amendment filed Nov. 10, 2008, 3 pgs.
U.S. Appl. No. 12/196,398, Preliminary Amendment filed Dec. 1, 2010, 12 pgs.
U.S. Appl. No. 12/196,398, Preliminary Amendment filed Dec. 9, 2008, 46 pgs.
U.S. Appl. No. 12/196,398, Response filed Oct. 29, 2010 to Restriction Requirement mailed Sep. 29, 2010, 2 pgs.
U.S. Appl. No. 12/196,398, Restriction Requirement mailed Sep. 29, 2010, 6 pgs.
U.S. Appl. No. 12/196,398, Supplemental Notice of Allowability mailed Mar. 9, 2011, 4 pgs.
U.S. Appl. No. 12/196,398, Supplemental Notice of Allowability mailed Apr. 15, 2011, 4 pgs.
U.S. Appl. No. 12/196,405, Examiner Interview Summary mailed Jun. 20, 2011, 3 pgs.
U.S. Appl. No. 12/196,405, Non Final Office Action mailed Apr. 11, 2011, 13 pgs.
U.S. Appl. No. 12/196,405, Notice of Allowance mailed Oct. 26, 2011, 11 pgs.
U.S. Appl. No. 12/196,405, Preliminary Amendment filed Nov. 10, 2008, 3 pgs.
U.S. Appl. No. 12/196,405, Response filed Mar. 16, 2011 to Restriction Requirement mailed Feb. 14, 2011, 1 pgs.
U.S. Appl. No. 12/196,405, Response filed Jul. 12, 2011 to Non Final Office Action mailed Apr. 11, 2011, 19 pgs.
U.S. Appl. No. 12/196,405, Restriction Requirement mailed Feb. 14, 2011, 6 pgs.
U.S. Appl. No. 12/196,405, Supplemental Amendment filed Oct. 3, 2011, 12 pgs.
U.S. Appl. No. 12/196,407, Examiner Interview Summary mailed Jul. 14, 2011, 3 pgs.
U.S. Appl. No. 12/196,407, Non Final Office Action mailed May 4, 2011, 11 pgs.
U.S. Appl. No. 12/196,407, Notice of Allowance mailed Oct. 26, 2011, 10 pgs.
U.S. Appl. No. 12/196,407, Preliminary Amendment filed Nov. 10, 2008, 3 pgs.
U.S. Appl. No. 12/196,407, Response filed Apr. 20, 2011 to Restriction Requirement mailed Mar. 22, 2011, 12 pgs.
U.S. Appl. No. 12/196,407, Response filed Aug. 2, 2011 to Non Final Office Action mailed May 4, 2011, 27 pgs.
U.S. Appl. No. 12/196,407, Restriction Requirement mailed Mar. 22, 2011, 6 pgs.
U.S. Appl. No. 12/196,407, Supplemental Response to Non Final Office Action filed Oct. 3, 2011, 18 pgs.
U.S. Appl. No. 12/196,410, Examiner Interview Summary mailed Jul. 14, 2011, 3 pgs.
U.S. Appl. No. 12/196,410, Non Final Office Action mailed May 9, 2011, 9 pgs.
U.S. Appl. No. 12/196,410, Notice of Allowance mailed Oct. 13, 2011, 8 pgs.
U.S. Appl. No. 12/196,410, Response filed Apr. 20, 2011 to Restriction Requirement mailed Mar. 22, 2011, 13 pgs.
U.S. Appl. No. 12/196,410, Response filed Aug. 1, 2011 to Non Final Office Action mailed May 9, 2011, 23 pgs.
U.S. Appl. No. 12/196,410, Restriction Requirement mailed Mar. 22, 2011, 6 pgs.
U.S. Appl. No. 12/196,410, Supplemental Amendment filed Oct. 3, 2011, 15 pgs.
U.S. Appl. No. 12/398,548, Examiner Interview Summary mailed Jul. 12, 2011, 3 pgs.
U.S. Appl. No. 12/398,548, Non Final Office Action mailed Apr. 12, 2011, 7 pgs.
U.S. Appl. No. 12/398,548, Notice of Allowance mailed Oct. 18, 2011, 7 pgs.
U.S. Appl. No. 12/398,548, Response filed Jul. 12, 2011 to Non Final Office Action mailed Apr. 12, 2011, 15 pgs.
U.S. Appl. No. 12/398,548, Supplemental Preliminary Amendment filed Sep. 7, 2010, 11 pgs.
U.S. Appl. No. 12/419,491, Examiner Interview Summary mailed May 30, 2012, 3 pgs.
U.S. Appl. No. 12/419,491, Examiner Interview Summary mailed Nov. 29, 2011, 3 pgs.
U.S. Appl. No. 12/419,491, Final Office Action mailed Apr. 12, 2012, 12 pgs.
U.S. Appl. No. 12/419,491, Non Final Office Action mailed Sep. 22, 2011, 12 pgs.
U.S. Appl. No. 12/419,491, Notice of Allowance mailed Jul. 13, 2012, 10 pgs.
U.S. Appl. No. 12/419,491, Response filed May 30, 2012 to Final Office Action mailed Apr. 12, 2012, 12 pgs.
U.S. Appl. No. 12/419,491, Response filed Dec. 9, 2011 to Non Final Office Action mailed Sep. 22, 2011, 17 pgs.
U.S. Appl. No. 12/474,802, Notice of Allowance mailed Aug. 31, 2011, 13 pgs.
U.S. Appl. No. 12/474,802, Notice of Allowance mailed Oct. 26, 2011, 4 pgs.
U.S. Appl. No. 12/474,802, Response filed Mar. 28, 2011 to Restriction Requirement mailed Feb. 24, 2011, 12 pgs.
U.S. Appl. No. 12/474,802, Restriction Requirement mailed Feb. 24, 2011, 6 pgs.
U.S. Appl. No. 12/489,168, Examiner Interview Summary mailed Feb. 21, 2012, 3 pgs.
U.S. Appl. No. 12/489,168, Non Final Office Action mailed Dec. 7, 2011, 10 pgs.
U.S. Appl. No. 12/489,168, Notice of Allowance mailed Apr. 26, 2012, 8 pgs.
U.S. Appl. No. 12/489,168, Notice of Allowance mailed Sep. 5, 2012, 8 pgs.
U.S. Appl. No. 12/489,168, Preliminary Amendment filed Oct. 22, 2009, 3 pgs.
U.S. Appl. No. 12/489,168, Response filed Feb. 27, 2012 to Non Final Office Action mailed Dec. 7, 2011, 15 pgs.
U.S. Appl. No. 12/489,168, Response filed Nov. 11, 2011 to Restriction Requirement mailed Oct. 20, 2011, 1 pg.
U.S. Appl. No. 12/489,168, Restriction Requirement mailed Oct. 20, 2011, 8 pgs.
U.S. Appl. No. 12/489,181, Examiner Interview Summary mailed Feb. 13, 2012, 3 pgs.
U.S. Appl. No. 12/489,181, Non Final Office Action mailed Jan. 3, 2012, 9 pgs.
U.S. Appl. No. 12/489,181, Notice of Allowance mailed May 23, 2012, 9 pgs.
U.S. Appl. No. 12/489,181, Preliminary Amendment filed Mar. 31, 2011, 10 pgs.
U.S. Appl. No. 12/489,181, Preliminary Amendment filed Oct. 22, 2009, 3 pgs.

(56) References Cited

OTHER PUBLICATIONS

U.S. Appl. No. 12/489,181, Response filed Mar. 27, 2012 to Non Final Office Action mailed Jan. 3, 2012, 12 pgs.
U.S. Appl. No. 12/489,181, Response filed Dec. 5, 2011 to Restriction Requirement mailed Nov. 4, 2011, 1 pg.
U.S. Appl. No. 12/489,181, Restriction Requirement mailed Nov. 4, 2011, 7 pgs.
U.S. Appl. No. 12/570,854, Examiner Interview Summary mailed Apr. 16, 2012, 3 pgs.
U.S. Appl. No. 12/570,854, Non Final Office Action mailed Feb. 10, 2012, 8 pgs.
U.S. Appl. No. 12/570,854, Notice of Allowance mailed Jun. 29, 2012, 10 pgs.
U.S. Appl. No. 12/570,854, Notice of Allowance mailed Sep. 19, 2012, 6 pgs.
U.S. Appl. No. 12/570,854, Response filed May 10, 2012 to Non Final Office Action mailed Feb. 10, 2012, 27 pgs.
U.S. Appl. No. 12/570,854, Response filed Dec. 20, 2011 to Restriction Requirement mailed Dec. 14, 2011, 1 pg.
U.S. Appl. No. 12/570,854, Restriction Requirement mailed Dec. 14, 2011, 6 pgs.
U.S. Appl. No. 12/702,067, Non Final Office Action mailed Mar. 5, 2013, 8 pgs.
U.S. Appl. No. 12/702,067, Notice of Allowance mailed Oct. 7, 2013, 11 pgs.
U.S. Appl. No. 12/702,067, Preliminary Amendment filed Jan. 11, 2011, 13 pgs.
U.S. Appl. No. 12/702,067, Response filed Jun. 5, 2013 to Non Final Office Action mailed Mar. 5, 2013, 17 pgs.
U.S. Appl. No. 12/702,067, Response filed Oct. 2, 2012 to Restriction Requirement mailed Sep. 4, 2012, 1 pg.
U.S. Appl. No. 12/702,067, Restriction Requirement mailed Sep. 4, 2012, 9 pgs.
U.S. Appl. No. 12/719,337, Advisory Action mailed Sep. 30, 2014, 4 pgs.
U.S. Appl. No. 12/719,337, Examiner Interview Summary mailed Apr. 4, 2014, 4 pgs.
U.S. Appl. No. 12/719,337, Examiner Interview Summary mailed May 14, 2013, 3 pgs.
U.S. Appl. No. 12/719,337, Examiner Interview Summary mailed Sep. 18, 2014, 3 pgs.
U.S. Appl. No. 12/719,337, Final Office Action mailed Mar. 12, 2013, 8 pgs.
U.S. Appl. No. 12/719,337, Final Office Action mailed Jul. 18, 2014, 15 pgs.
U.S. Appl. No. 12/719,337, Non Final Office Action mailed Jan. 10, 2014, 14 pgs.
U.S. Appl. No. 12/719,337, Non Final Office Action mailed Sep. 5, 2012, 7 pgs.
U.S. Appl. No. 12/719,337, Notice of Allowance mailed Mar. 11, 2015, 10 pgs.
U.S. Appl. No. 12/719,337, Notice of Non-Compliant Amendment mailed May 2, 2014, 3 pgs.
U.S. Appl. No. 12/719,337, Response filed Apr. 10, 2014 to Non Final Office Action mailed Jan. 10, 2014, 16 pgs.
U.S. Appl. No. 12/719,337, Response filed May 25, 2012 to Restriction Requirement mailed Apr. 26, 2012, 9 pgs.
U.S. Appl. No. 12/719,337, Response filed Jun. 5, 2013 to Final Office Action mailed Mar. 12, 2013, 16 pgs.
U.S. Appl. No. 12/719,337, Response filed Jun. 25, 2014 to Notice of Non-Compliant Amendment mailed May 2, 2014, 10 pgs.
U.S. Appl. No. 12/719,337, Response filed Sep. 18, 2014 to Final Office Action mailed Jul. 18, 2014, 13 pgs.
U.S. Appl. No. 12/719,337, Response filed Nov. 28, 2012 to Non Final Office Action mailed Sep. 5, 2012, 14 pgs.
U.S. Appl. No. 12/719,337, Restriction Requirement mailed Apr. 26, 2012, 8 pgs.
U.S. Appl. No. 12/788,973, Advisory Action mailed Jan. 23, 2013, 3 pgs.
U.S. Appl. No. 12/788,973, Advisory Action mailed Dec. 27, 2012, 8 pgs.
U.S. Appl. No. 12/788,973, Final Office Action mailed Sep. 18, 2012, 16 pgs.
U.S. Appl. No. 12/788,973, Non Final Office Action mailed May 8, 2012, 12 pgs.
U.S. Appl. No. 12/788,973, Notice of Allowance mailed Mar. 21, 2013, 6 pgs.
U.S. Appl. No. 12/788,973, Response filed Jan. 16, 2013 to Advisory Action mailed Dec. 27, 2012, 9 pgs.
U.S. Appl. No. 12/788,973, Response filed Jul. 19, 2012 to Non Final Office Action mailed May 8, 2012, 21 pgs.
U.S. Appl. No. 12/788,973, Response filed Dec. 16, 2011 to Restriction Requirement mailed Dec. 6, 2011, 11 pgs.
U.S. Appl. No. 12/788,973, Response filed Dec. 17, 2012 to Final Office Action mailed Sep. 18, 2012, 15 pgs.
U.S. Appl. No. 12/788,973, Restriction Requirement mailed Dec. 6, 2011, 9 pgs.
U.S. Appl. No. 12/788,973, Supplemental Notice of Allowance mailed May 24, 2013, 2 pgs.
U.S. Appl. No. 12/788,978, Advisory Action mailed Dec. 24, 2013, 4 pgs.
U.S. Appl. No. 12/788,978, Applicant's Summary of Examiner Interview filed Dec. 12, 2013, 2 pgs.
U.S. Appl. No. 12/788,978, Corrected Notice of Allowance mailed Apr. 30, 2014, 2 pgs.
U.S. Appl. No. 12/788,978, Examiner Interview Summary mailed Jan. 28, 2014, 3 pgs.
U.S. Appl. No. 12/788,978, Examiner Interview Summary mailed Mar. 22, 2013, 3 pgs.
U.S. Appl. No. 12/788,978, Examiner Interview Summary mailed Sep. 11, 2012, 3 pgs.
U.S. Appl. No. 12/788,978, Examiner Interview Summary mailed Oct. 29, 2013, 4 pgs.
U.S. Appl. No. 12/788,978, Examiner Interview Summary mailed Dec. 16, 2013, 3 pgs.
U.S. Appl. No. 12/788,978, Examiner Interview Summary mailed Dec. 27, 2012, 3 pgs.
U.S. Appl. No. 12/788,978, Final Office Action mailed Aug. 20, 2013, 17 pgs.
U.S. Appl. No. 12/788,978, Final Office Action mailed Nov. 2, 2012, 14 pgs.
U.S. Appl. No. 12/788,978, Non Final Office Action mailed Jan. 11, 2013, 16 pgs.
U.S. Appl. No. 12/788,978, Non Final Office Action mailed Jul. 13, 2012, 17 pgs.
U.S. Appl. No. 12/788,978, Notice of Allowance mailed Jan. 24, 2014, 9 pgs.
U.S. Appl. No. 12/788,978, Notice of Non-Compliant Amendment mailed Jun. 6, 2013, 3 pgs.
U.S. Appl. No. 12/788,978, Response filed Jan. 2, 2013 to Final Office Action mailed Nov. 2, 2012, 13 pgs.
U.S. Appl. No. 12/788,978, Response filed Jan. 20, 2014 to Advisory Action mailed Dec. 24, 2013, 4 pgs.
U.S. Appl. No. 12/788,978, Response filed Apr. 8, 2013 to Non Final Office Action mailed Jan. 11, 2013, 16 pgs.
U.S. Appl. No. 12/788,978, Response filed May 21, 2012 to Restriction Requirement mailed Apr. 20, 2012, 12 pgs.
U.S. Appl. No. 12/788,978, Response filed Jul. 3, 2013 to Notice of Non-Compliant Amendment mailed Jun. 6, 2013, 17 pgs.
U.S. Appl. No. 12/788,978, Response filed Oct. 5, 2012 to Non Final Office Action mailed Jul. 13, 2012, 20 pgs.
U.S. Appl. No. 12/788,978, Response filed Nov. 20, 2013 to Final Office Action mailed Aug. 20, 2013, 15 pgs.
U.S. Appl. No. 12/788,978, Restriction Requirement mailed Apr. 20, 2012, 8 pgs.
U.S. Appl. No. 12/828,977, Examiner Interview Summary mailed Jul. 9, 2012, 3 pgs.
U.S. Appl. No. 12/828,977, Non Final Office Action mailed May 3, 2012, 9 pgs.
U.S. Appl. No. 12/828,977, Notice of Allowance mailed Sep. 5, 2012, 9 pgs.

(56) References Cited

OTHER PUBLICATIONS

U.S. Appl. No. 12/828,977, Preliminary Amendment filed Jul. 19, 2011, 10 pgs.
U.S. Appl. No. 12/828,977, Response filed Mar. 14, 2012 to Restriction Requirement mailed Feb. 13, 2012, 9 pgs.
U.S. Appl. No. 12/828,977, Response filed Jul. 25, 2012 to Non Final Office Action mailed May 3, 2012, 11 pgs.
U.S. Appl. No. 12/828,977, Restriction Requirement mailed Feb. 13, 2012, 7 pgs.
U.S. Appl. No. 12/915,962, Examiner Interview Summary mailed Jul. 25, 2012, 3 pgs.
U.S. Appl. No. 12/915,962, Non Final Office Action mailed May 7, 2012, 11 pgs.
U.S. Appl. No. 12/915,962, Non Final Office Action mailed Oct. 15, 2012, 9 pgs.
U.S. Appl. No. 12/915,962, Notice of Allowance mailed Jun. 10, 2013, 12 pgs.
U.S. Appl. No. 12/915,962, Response filed Jan. 10, 2013 to Non Final Office Action mailed Oct. 15, 2012, 21 pgs.
U.S. Appl. No. 12/915,962, Response filed Mar. 16, 2012 to Restriction Requirement mailed Feb. 15, 2012, 15 pgs.
U.S. Appl. No. 12/915,962, Response filed Aug. 7, 2012 to Non Final Office Action mailed May 7, 2012, 26 pgs.
U.S. Appl. No. 12/915,962, Restriction Requirement mailed Feb. 15, 2012, 8 pgs.
U.S. Appl. No. 12/938,902, Examiner Interview Summary mailed Dec. 3, 2012, 3 pgs.
U.S. Appl. No. 12/976,328, Examiner Interview Summary mailed Feb. 13, 2012, 3 pgs.
U.S. Appl. No. 12/976,328, Non Final Office Action mailed Dec. 15, 2011, 13 pgs.
U.S. Appl. No. 12/976,328, Notice of Allowance mailed Apr. 30, 2012, 9 pgs.
U.S. Appl. No. 12/976,328, Response filed Mar. 2, 2012 to Non Final Office Action mailed Dec. 15, 2011, 15 pgs.
U.S. Appl. No. 13/045,689, Examiner Interview Summary mailed May 14, 2012, 3 pgs.
U.S. Appl. No. 13/045,689, Non Final Office Action mailed Mar. 20, 2012, 11 pgs.
U.S. Appl. No. 13/045,689, Notice of Allowance mailed Aug. 10, 2012, 10 pgs.
U.S. Appl. No. 13/045,689, Notice of Allowance mailed Sep. 24, 2012, 7 pgs.
U.S. Appl. No. 13/045,689, Response filed Jan. 30, 2012 to Restriction Requirement mailed Dec. 29, 2011, 13 pgs.
U.S. Appl. No. 13/045,689, Response filed Jun. 8, 2012 to Non Final Office Action mailed Mar. 20, 2012, 15 pgs.
U.S. Appl. No. 13/045,689, Restriction Requirement mailed Dec. 29, 2011, 6 pgs.
U.S. Appl. No. 13/045,691, Examiner Interview Summary mailed May 14, 2012, 3 pgs.
U.S. Appl. No. 13/045,691, Non Final Office Action mailed Mar. 20, 2012, 12 pgs.
U.S. Appl. No. 13/045,691, Notice of Allowance mailed Jun. 19, 2012, 10 pgs.
U.S. Appl. No. 13/045,691, Response filed Feb. 9, 2012 to Restriction Requirement mailed Jan. 9, 2012, 1 pg.
U.S. Appl. No. 13/045,691, Response filed Jun. 8, 2012 to Non Final Office Action mailed Mar. 20, 2012, 17 pgs.
U.S. Appl. No. 13/045,691, Restriction Requirement mailed Jan. 9, 2012, 6 pgs.
U.S. Appl. No. 13/071,563, Final Office Action mailed May 23, 2014, 13 pgs.
U.S. Appl. No. 13/071,563, Non Final Office Action mailed Oct. 23, 2013, 18 pgs.
U.S. Appl. No. 13/071,563, Notice of Allowance mailed Aug. 15, 2014, 7 pgs.
U.S. Appl. No. 13/071,563, Preliminary Amendment filed May 1, 2012, 8 pgs.
U.S. Appl. No. 13/071,563, Preliminary Amendment filed Dec. 6, 2011, 7 pgs.
U.S. Appl. No. 13/071,563, Response filed Jan. 21, 2014 to Non Final Office Action mailed Oct. 23, 2013, 13 pgs.
U.S. Appl. No. 13/071,563, Response filed Jul. 23, 2014 to Final Office Action mailed May 23, 2014, 14 pgs.
U.S. Appl. No. 13/071,563, Response filed Sep. 19, 2013 to Restriction Requirement mailed Aug. 19, 2013, 11 pgs.
U.S. Appl. No. 13/071,563, Restriction Requirement mailed Aug. 19, 2013, 7 pgs.
U.S. Appl. No. 13/098,897, Examiner Interview Summary mailed Nov. 27, 2012, 3 pgs.
U.S. Appl. No. 13/098,897, Non Final Office Action mailed Sep. 21, 2012, 9 pgs.
U.S. Appl. No. 13/098,897, Notice of Allowance mailed Jun. 11, 2013, 13 pgs.
U.S. Appl. No. 13/098,897, Response filed Aug. 30, 2012 to Restriction Requirement mailed Jul. 30, 2012, 16 pgs.
U.S. Appl. No. 13/098,897, Response filed Dec. 18, 2012 to Non Final Office Action mailed Sep. 21, 2012, 21 pgs.
U.S. Appl. No. 13/098,897, Restriction Requirement mailed Jul. 30, 2012, 8 pgs.
U.S. Appl. No. 13/098,927, Advisory Action mailed Aug. 8, 2013, 3 pgs.
U.S. Appl. No. 13/098,927, Applicant's Summary of Examiner Interview filed Sep. 23, 2013, 12 pgs.
U.S. Appl. No. 13/098,927, Examiner Interview Summary mailed Jun. 28, 2013, 3 pgs.
U.S. Appl. No. 13/098,927, Examiner Interview Summary mailed Sep. 20, 2013, 3 pgs.
U.S. Appl. No. 13/098,927, Final Office Action mailed May 22, 2013, 10 pgs.
U.S. Appl. No. 13/098,927, Non Final Office Action mailed Sep. 24, 2012, 12 pgs.
U.S. Appl. No. 13/098,927, Notice of Allowance mailed Jan. 8, 2014, 5 pgs.
U.S. Appl. No. 13/098,927, Notice of Allowance mailed Sep. 26, 2013, 14 pgs.
U.S. Appl. No. 13/098,927, Response filed Jul. 22, 2015 to Final Office Action mailed May 22, 2013, 17 pgs.
U.S. Appl. No. 13/098,927, Response filed Aug. 27, 2012 to Restriction Requirement mailed Jul. 25, 2012, 14 pgs.
U.S. Appl. No. 13/098,927, Response filed Dec. 21, 2012 to Non Final Office Action mailed Sep. 24, 2012, 21 pgs.
U.S. Appl. No. 13/098,927, Restriction Requirement mailed Jul. 25, 2012, 8 pgs.
U.S. Appl. No. 13/102,182, Notice of Allowance mailed Mar. 22, 2012, 10 pgs.
U.S. Appl. No. 13/109,667, Advisory Action mailed Feb. 4, 2014, 4 pgs.
U.S. Appl. No. 13/109,667, Examiner Interview Summary mailed Dec. 20, 2013, 3 pgs.
U.S. Appl. No. 13/109,667, Final Office Action mailed Oct. 11, 2013, 19 pgs.
U.S. Appl. No. 13/109,667, Non Final Office Action mailed May 21, 2013, 21 pgs.
U.S. Appl. No. 13/109,667, Notice of Allowance mailed Feb. 18, 2014, 10 pgs.
U.S. Appl. No. 13/109,667, Response filed Jan. 13, 2014 to Final Office Action mailed Oct. 11, 2013, 20 pgs.
U.S. Appl. No. 13/109,667, Response filed May 2, 2013 to Restriction Requirement mailed Apr. 2, 2013, 1 pg.
U.S. Appl. No. 13/109,667, Response filed Aug. 21, 2013 to Non Final Office Action mailed May 21, 2013, 27 pgs.
U.S. Appl. No. 13/109,667, Restriction Requirement mailed Apr. 2, 2013, 8 pgs.
U.S. Appl. No. 13/109,667, Supplemental Notice of Allowability mailed Jun. 12, 2014, 3 pgs.
U.S. Appl. No. 13/109,667, Supplemental Notice of Allowance mailed May 28, 2014, 2 pgs.
U.S. Appl. No. 13/109,667, Supplemental Preliminary Amendment filed Feb. 4, 2014, 16 pgs.

(56) References Cited

OTHER PUBLICATIONS

U.S. Appl. No. 13/109,672, 312 Amendment filed Jan. 15, 2015, 3 pgs.
U.S. Appl. No. 13/109,672, Non Final Office Action mailed May 15, 2014, 10 pgs.
U.S. Appl. No. 13/109,672, Notice of Allowance mailed Feb. 3, 2015, 2 pgs.
U.S. Appl. No. 13/109,672, Notice of Allowance mailed Sep. 29, 2014, 9 pgs.
U.S. Appl. No. 13/109,672, PTO Response to Rule 312 Communication mailed Jan. 27, 2015, 2 pgs.
U.S. Appl. No. 13/109,672, Response filed Apr. 14, 2014 to Restriction Requirement mailed Feb. 14, 2014, 15 pgs.
U.S. Appl. No. 13/109,672, Response filed Aug. 15, 2014 to Non Final Office Action mailed May 15, 2014, 20 pgs.
U.S. Appl. No. 13/109,672, Response filed Nov. 4, 2013 to Restriction Requirement mailed Oct. 2, 2013, 10 pgs.
U.S. Appl. No. 13/109,672, Restriction Requirement mailed Feb. 14, 2014, 7 pgs.
U.S. Appl. No. 13/109,672, Restriction Requirement mailed Oct. 2, 2013, 7 pgs.
U.S. Appl. No. 13/111,564, Corrected Notice of Allowance mailed Oct. 9, 2013, 2 pgs.
U.S. Appl. No. 13/111,564, Examiner Interview Summary mailed Jun. 18, 2013, 3 pgs.
U.S. Appl. No. 13/111,564, Non Final Office Action mailed Mar. 18, 2013, 8 pgs.
U.S. Appl. No. 13/111,564, Notice of Allowance mailed Jun. 28, 2013, 12 pgs.
U.S. Appl. No. 13/111,564, Response filed Feb. 4, 2013 to Restriction Requirement mailed Jan. 3, 2013, 20 pgs.
U.S. Appl. No. 13/111,564, Response filed Jun. 18, 2013 to Non Final Office Action mailed Mar. 18, 2013, 25 pgs.
U.S. Appl. No. 13/111,564, Restriction Requirement mailed Jan. 3, 2013, 5 pgs.
U.S. Appl. No. 13/177,153, Final Office Action mailed May 28, 2013, 11 pgs.
U.S. Appl. No. 13/177,153, Non Final Office Action mailed Oct. 2, 2012, 11 pgs.
U.S. Appl. No. 13/177,153, Notice of Allowance mailed Jan. 7, 2014, 4 pgs.
U.S. Appl. No. 13/177,153, Notice of Allowance mailed Sep. 17, 2013, 13 pgs.
U.S. Appl. No. 13/177,153, Response filed Aug. 28, 2013 to Final Office Action mailed May 28, 2013, 19 pgs.
U.S. Appl. No. 13/177,153, Response filed Sep. 4, 2012 to Restriction Requirement mailed Aug. 2, 2012, 15 pgs.
U.S. Appl. No. 13/177,153, Response filed Dec. 20, 2012 to Non Final Office Action mailed Oct. 2, 2012, 16 pgs.
U.S. Appl. No. 13/177,153, Restriction Requirement mailed Aug. 2, 2012, 9 pgs.
U.S. Appl. No. 13/181,729, Examiner Interview Summary mailed May 9, 2013, 3 pgs.
U.S. Appl. No. 13/181,729, Final Office Action mailed Mar. 13, 2013, 14 pgs.
U.S. Appl. No. 13/181,729, Non Final Office Action mailed Oct. 2, 2012, 7 pgs.
U.S. Appl. No. 13/181,729, Notice of Allowance mailed May 23, 2013, 9 pgs.
U.S. Appl. No. 13/181,729, Response filed May 13, 2013 to Final Office Action mailed Mar. 13, 2013, 13 pgs.
U.S. Appl. No. 13/181,729, Response filed Dec. 20, 2012 to Non Final Office Action mailed Oct. 2, 2012, 15 pgs.
U.S. Appl. No. 13/269,097, Final Office Action mailed Aug. 8, 2013, 7 pgs.
U.S. Appl. No. 13/269,097, Non Final Office Action mailed Feb. 12, 2013, 10 pgs.
U.S. Appl. No. 13/269,097, Notice of Allowance mailed Feb. 3, 2014, 5 pgs.
U.S. Appl. No. 13/269,097, Notice of Allowance mailed Oct. 21, 2013, 9 pgs.
U.S. Appl. No. 13/269,097, Response filed May 13, 2013 to Non Final Office Action mailed Feb. 12, 2013, 17 pgs.
U.S. Appl. No. 13/269,097, Response filed Oct. 8, 2013 to Final Office Action mailed Aug. 8, 2013, 12 pgs.
U.S. Appl. No. 13/269,097, Response filed Nov. 13, 2012 to Restriction Requirement mailed Oct. 17, 2012, 1 pg.
U.S. Appl. No. 13/269,097, Restriction Requirement mailed Oct. 17, 2012, 8 pgs.
U.S. Appl. No. 13/278,341, Notice of Allowance mailed Jun. 18, 2013, 10 pgs.
U.S. Appl. No. 13/278,341, Response filed Mar. 8, 2013 to Restriction Requirement mailed Feb. 11, 2013, 1 pg.
U.S. Appl. No. 13/278,341, Restriction Requirement mailed Feb. 11, 2013, 6 pgs.
U.S. Appl. No. 13/281,009, Non Final Office Action mailed Jun. 2, 2015, 9 pgs.
U.S. Appl. No. 13/281,009, Notice of Allowance mailed Feb. 24, 2016, 9 pgs.
U.S. Appl. No. 13/281,009, Notice of Allowance mailed Oct. 29, 2015, 8 pgs.
U.S. Appl. No. 13/281,009, Response filed Sep. 2, 2015 to Non Final Office Action mailed Jun. 2, 2015, 13 pgs.
U.S. Appl. No. 13/281,009, Restriction Requirement mailed Feb. 11, 2015, 6 pgs.
U.S. Appl. No. 13/288,459, Examiner Interview Summary mailed Feb. 6, 2015, 3 pgs.
U.S. Appl. No. 13/288,459, Non Final Office Action mailed Jun. 24, 2015, 10 pgs.
U.S. Appl. No. 13/288,459, Non Final Office Action mailed Nov. 4, 2014, 15 pgs.
U.S. Appl. No. 13/288,459, Notice of Allowance mailed Jan. 11, 2016, 13 pgs.
U.S. Appl. No. 13/288,459, Response filed Mar. 3, 2015 to Non Final Office Action mailed Nov. 4, 2014, 16 pgs.
U.S. Appl. No. 13/288,459, Response filed Oct. 13, 2014 to Restriction Requirement mailed Aug. 11, 2014, 15 pgs.
U.S. Appl. No. 13/288,459, Response filed Oct. 23, 2015 to Non Final Office Action mailed Jun. 24, 2015, 14 pgs.
U.S. Appl. No. 13/288,459, Restriction Requirement mailed Aug. 11, 2014, 9 pgs.
U.S. Appl. No. 13/288,463, Examiner Interview Summary mailed Jun. 3, 2014, 3 pgs.
U.S. Appl. No. 13/288,463, Non Final Office Action mailed Feb. 24, 2014, 13 pgs.
U.S. Appl. No. 13/288,463, Notice of Allowance mailed Aug. 27, 2014, 9 pgs.
U.S. Appl. No. 13/288,463, Response filed May 27, 2014 to Non Final Office Action mailed Feb. 24, 2014, 15 pgs.
U.S. Appl. No. 13/288,463, Supplemental Notice of Allowability mailed Dec. 8, 2014, 5 pgs.
U.S. Appl. No. 13/288,463, Supplemental Notice of Allowability mailed Dec. 19, 2014, 5 pgs.
U.S. Appl. No. 13/293,825, Notice of Allowability mailed Jun. 22, 2015, 7 pgs.
U.S. Appl. No. 13/293,825, Notice of Allowance mailed May 19, 2015, 9 pgs.
U.S. Appl. No. 13/293,825, Response filed Apr. 15, 2015 to Restriction Requirement mailed Feb. 12, 2015, 17 pgs.
U.S. Appl. No. 13/293,825, Restriction Requirement mailed Feb. 12, 2015, 9 pgs.
U.S. Appl. No. 13/295,126, Non Final Office Action mailed May 19, 2015, 9 pgs.
U.S. Appl. No. 13/295,126, Notice of Allowance mailed Oct. 22, 2015, 9 pgs.
U.S. Appl. No. 13/295,126, Response filed Apr. 13, 2015 to Restriction Requirement mailed Feb. 12, 2015, 1 pgs.
U.S. Appl. No. 13/295,126, Response filed Aug. 17, 2015 to Non Final Office Action mailed May 19, 2015, 21 pgs.
U.S. Appl. No. 13/295,126, Restriction Requirement mailed Feb. 12, 2015, 9 pgs.

(56) References Cited

OTHER PUBLICATIONS

U.S. Appl. No. 13/311,936, Examiner Interview Summary mailed Feb. 12, 2015, 2 pgs.
U.S. Appl. No. 13/311,936, Non Final Office Action mailed Feb. 9, 2015, 13 pgs.
U.S. Appl. No. 13/311,936, Non Final Office Action mailed Oct. 19, 2015, 8 pgs.
U.S. Appl. No. 13/311,936, Response filed Jan. 18, 2016 to Non Final Office Action mailed Oct. 19, 2015, 8 pgs.
U.S. Appl. No. 13/311,936, Response filed Jun. 9, 2015 to Non Final Office Action mailed Feb. 9, 2015, 12 pgs.
U.S. Appl. No. 13/311,936, Response filed Oct. 3, 2014 to Restriction Requirement mailed Aug. 5, 2014, 10 pgs.
U.S. Appl. No. 13/311,936, Restriction Requirement mailed Aug. 5, 2014, 7 pgs.
U.S. Appl. No. 13/350,985, Final Office Action mailed Apr. 16, 2015, 8 pgs.
U.S. Appl. No. 13/350,985, Non Final Office Action mailed Dec. 15, 2014, 8 pgs.
U.S. Appl. No. 13/350,985, Notice of Allowance mailed Jul. 27, 2015, 5 pgs.
U.S. Appl. No. 13/350,985, Response filed Mar. 13, 2015 to Non Final Office Action mailed Dec. 15, 2014, 10 pgs.
U.S. Appl. No. 13/350,985, Response filed Jul. 9, 2015 to Final Office Action mailed Apr. 16, 2015, 8 pgs.
U.S. Appl. No. 13/350,985, Response filed Dec. 2, 2014 to Restriction Requirement mailed Oct. 2, 2014, 9 pgs.
U.S. Appl. No. 13/350,985, Restriction Requirement mailed Oct. 2, 2014, 6 pgs.
U.S. Appl. No. 13/399,125, Corrected Notice of Allowance mailed Aug. 28, 2014, 2 pgs.
U.S. Appl. No. 13/399,125, Examiner Interview Summary mailed May 17, 2013, 3 pgs.
U.S. Appl. No. 13/399,125, Final Office Action mailed Mar. 20, 2013, 12 pgs.
U.S. Appl. No. 13/399,125, Non Final Office Action mailed Oct. 24, 2012, 12 pgs.
U.S. Appl. No. 13/399,125, Notice of Allowance mailed May 16, 2014, 8 pgs.
U.S. Appl. No. 13/399,125, Response filed Jan. 10, 2013 to Non Final Office Action mailed Oct. 24, 2012, 15 pgs.
U.S. Appl. No. 13/399,125, Response filed May 20, 2013 to Final Office Action mailed Mar. 20, 2013, 14 pgs.
U.S. Appl. No. 13/412,105, Advisory Action mailed Feb. 24, 2014, 3 pgs.
U.S. Appl. No. 13/412,105, Examiner Interview Summary mailed Feb. 6, 2014, 3 pgs.
U.S. Appl. No. 13/412,105, Examiner Interview Summary mailed Oct. 11, 2013, 3 pgs.
U.S. Appl. No. 13/412,105, Final Office Action mailed Dec. 13, 2013, 9 pgs.
U.S. Appl. No. 13/412,105, Non Final Office Action mailed Jul. 15, 2013, 10 pgs.
U.S. Appl. No. 13/412,105, Notice of Allowance mailed Aug. 18, 2014, 9 pgs.
U.S. Appl. No. 13/412,105, Response filed Feb. 10, 2014 to Final Office Action mailed Dec. 13, 2013, 14 pgs.
U.S. Appl. No. 13/412,105, Response filed Mar. 13, 2014 to Advisory Action mailed Feb. 24, 2014, 19 pgs.
U.S. Appl. No. 13/412,105, Response filed May 6, 2013 to Restriction Requirement mailed Apr. 5, 2013, 9 pgs.
U.S. Appl. No. 13/412,105, Response filed Oct. 14, 2013 to Non Final Office Action mailed Jul. 15, 2013, 13 pgs.
U.S. Appl. No. 13/412,105, Restriction Requirement mailed Apr. 5, 2013, 9 pgs.
U.S. Appl. No. 13/412,116, Corrected Notice of Allowance mailed Jun. 2, 2014, 2 pgs.
U.S. Appl. No. 13/412,116, Examiner Interview Summary mailed Dec. 13, 2013, 3 pgs.
U.S. Appl. No. 13/412,116, Non Final Office Action mailed Sep. 11, 2013, 9 pgs.
U.S. Appl. No. 13/412,116, Notice of Allowance mailed Feb. 19, 2014, 9 pgs.
U.S. Appl. No. 13/412,116, Response filed Jul. 3, 2013 to Restriction Requirement mailed Jun. 19, 2013, 1 pg.
U.S. Appl. No. 13/412,116, Response filed Dec. 11, 2013 to Non Final Office Action mailed Sep. 11, 2013, 11 pgs.
U.S. Appl. No. 13/412,116, Restriction Requirement mailed Jun. 19, 2013, 9 pgs.
U.S. Appl. No. 13/412,127, Examiner Interview Summary mailed Nov. 5, 2013, 3 pgs.
U.S. Appl. No. 13/412,127, Non Final Office Action mailed Aug. 7, 2013, 15 pgs.
U.S. Appl. No. 13/412,127, Notice of Allowance mailed Dec. 24, 2013, 10 pgs.
U.S. Appl. No. 13/412,127, Response filed May 23, 2013 to Restriction Requirement mailed Apr. 24, 2013, 2 pgs.
U.S. Appl. No. 13/412,127, Response filed Nov. 5, 2013 to Non Final Office Action mailed Aug. 7, 2013, 16 pgs.
U.S. Appl. No. 13/412,127, Restriction Requirement mailed Apr. 24, 2013, 10 pgs.
U.S. Appl. No. 13/587,374, Final Office Action mailed Nov. 6, 2013, 9 pgs.
U.S. Appl. No. 13/587,374, Non Final Office Action mailed Jul. 17, 2013, 8 pgs.
U.S. Appl. No. 13/587,374, Notice of Allowance mailed Feb. 28, 2014, 5 pgs.
U.S. Appl. No. 13/587,374, Preliminary Amendment filed Jun. 21, 2013, 9 pgs.
U.S. Appl. No. 13/587,374, Response filed Jan. 24, 2014 to Final Office Action mailed Nov. 6, 2013, 15 pgs.
U.S. Appl. No. 13/587,374, Response filed Oct. 14, 2013 to Non Final Office Action mailed Jul. 17, 2013, 14 pgs.
U.S. Appl. No. 13/625,413, Final Office Action mailed Oct. 30, 2015, 8 pgs.
U.S. Appl. No. 13/625,413, Non Final Office Action mailed Jun. 8, 2015, 11 pgs.
U.S. Appl. No. 13/625,413, Notice of Allowance mailed Dec. 11, 2015, 9 pgs.
U.S. Appl. No. 13/625,413, Response filed May 11, 2015 to Restriction Requirement mailed Mar. 10, 2015, 1 pg.
U.S. Appl. No. 13/625,413, Response filed Sep. 8, 2015 to Non Final Office Action mailed Jun. 8, 2015, 16 pgs.
U.S. Appl. No. 13/625,413, Response filed Dec. 1, 2015 to Final Office Action mailed Oct. 30, 2015, 9 pgs.
U.S. Appl. No. 13/625,413, Restriction Requirement mailed Mar. 10, 2015, 7 pgs.
U.S. Appl. No. 13/645,964, Advisory Action mailed Feb. 4, 2016, 2 pgs.
U.S. Appl. No. 13/645,964, Final Office Action mailed Oct. 6, 2015, 17 pgs.
U.S. Appl. No. 13/645,964, Non Final Office Action mailed Mar. 15, 2016, 15 pgs.
U.S. Appl. No. 13/645,964, Non Final Office Action mailed Mar. 17, 2015, 15 pgs.
U.S. Appl. No. 13/645,964, Response filed Jul. 17, 2015 to Non Final Office Action mailed Mar. 17, 2015, 17 pgs.
U.S. Appl. No. 13/645,964, Response filed Dec. 4, 2015 to Final Office Action mailed Oct. 6, 2015, 14 pgs.
U.S. Appl. No. 13/656,821, Notice of Allowance mailed Jun. 18, 2015, 11 pgs.
U.S. Appl. No. 13/656,821, Response filed May 11, 2015 to Restriction Requirement mailed Mar. 10, 2015, 1 pg.
U.S. Appl. No. 13/656,821, Restriction Requirement mailed Mar. 10, 2015, 6 pgs.
U.S. Appl. No. 13/720,648, Final Office Action mailed Nov. 16, 2015, 7 pgs.
U.S. Appl. No. 13/720,648, Non Final Office Action mailed Jun. 10, 2015, 11 pgs.
U.S. Appl. No. 13/720,648, Notice of Allowance mailed Feb. 5, 2016, 11 pgs.

(56) References Cited

OTHER PUBLICATIONS

U.S. Appl. No. 13/720,648, Response filed Jan. 13, 2016 to Final Office Action mailed Nov. 16, 2015, 9 pgs.
U.S. Appl. No. 13/720,648, Response filed May 11, 2015 to Restriction Requirement mailed Mar. 10, 2015, 8 pgs.
U.S. Appl. No. 13/720,648, Response filed Oct. 9, 2015 to Non Final Office Action mailed Jun. 10, 2015, 12 pgs.
U.S. Appl. No. 13/720,648, Restriction Requirement mailed Mar. 10, 2015, 8 pgs.
U.S. Appl. No. 13/721,970, Notice of Allowance mailed Aug. 12, 2013, 13 pgs.
U.S. Appl. No. 13/721,970, Preliminary Amendment filed Mar. 15, 2013, 13 pgs.
U.S. Appl. No. 13/721,970, Response filed May 8, 2013 to Restriction Requirement mailed Apr. 11, 2013, 1 pgs.
U.S. Appl. No. 13/721,970, Restriction Requirement mailed Apr. 11, 2013, 6 pgs.
U.S. Appl. No. 13/751,846, Final Office Action mailed Nov. 17, 2015, 9 pgs.
U.S. Appl. No. 13/751,846, Non Final Office Action mailed Jun. 15, 2015, 10 pgs.
U.S. Appl. No. 13/751,846, Notice of Allowance mailed Mar. 16, 2016, 11 pgs.
U.S. Appl. No. 13/751,846, Response filed Feb. 5, 2016 to Final Office Action mailed Nov. 17, 2015, 14 pgs.
U.S. Appl. No. 13/751,846, Response filed May 11, 2015 to Restriction Requirement mailed Mar. 10, 2015, 15 pgs.
U.S. Appl. No. 13/751,846, Response filed Oct. 9, 2015 to Non Final Office Action mailed Jun. 15, 2015, 20 pgs.
U.S. Appl. No. 13/751,846, Restriction Requirement mailed Mar. 10, 2015, 7 pgs.
U.S. Appl. No. 13/757,003, Non Final Office Action mailed Jun. 25, 2015, 8 pgs.
U.S. Appl. No. 13/757,003, Notice of Allowance mailed Feb. 8, 2016, 10 pgs.
U.S. Appl. No. 13/757,003, Response filed May 12, 2015 to Restriction Requirement mailed Mar. 12, 2015, 9 pgs.
U.S. Appl. No. 13/757,003, Response filed Oct. 26, 2015 to Non Final Office Action mailed Jul. 25, 2015, 8 pgs.
U.S. Appl. No. 13/757,003, Restriction Requirement mailed Mar. 12, 2015, 6 pgs.
U.S. Appl. No. 13/757,019, Non Final Office Action mailed Jun. 25, 2015, 11 pgs.
U.S. Appl. No. 13/757,019, Notice of Allowance mailed Dec. 10, 2015, 10 pgs.
U.S. Appl. No. 13/757,019, Response filed May 11, 2015 to Restriction Requirement mailed Mar. 11, 2015, 9 pgs.
U.S. Appl. No. 13/757,019, Response filed Oct. 26, 2015 to Non Final Office Action mailed Jun. 25, 2015, 9 pgs.
U.S. Appl. No. 13/757,019, Restriction Requirement mailed Mar. 11, 2015, 10 pgs.
U.S. Appl. No. 13/790,982, Examiner Interview Summary mailed Jun. 9, 2015, 3 pgs.
U.S. Appl. No. 13/790,982, Non Final Office Action mailed Sep. 16, 2015, 11 pgs.
U.S. Appl. No. 13/790,982, Notice of Allowance mailed Feb. 24, 2016, 10 pgs.
U.S. Appl. No. 13/790,982, Response filed Jun. 2, 2015 to Restriction Requirement mailed Apr. 2, 2015, 11 pgs.
U.S. Appl. No. 13/790,982, Response filed Dec. 16, 2015 to Non Final Office Action mailed Sep. 16, 2015, 10 pgs.
U.S. Appl. No. 13/790,982, Restriction Requirement mailed Apr. 2, 2015, 10 pgs.
U.S. Appl. No. 13/790,997, Examiner Interview Summary mailed Jun. 8, 2015, 3 pgs.
U.S. Appl. No. 13/790,997, Non Final Office Action mailed Sep. 21, 2015, 8 pgs.
U.S. Appl. No. 13/790,997, Notice of Allowance mailed Mar. 2, 2016, 9 pgs.
U.S. Appl. No. 13/790,997, Response filed Jun. 2, 2015 to Restriction Requirement mailed Apr. 2, 2015, 12 pgs.
U.S. Appl. No. 13/790,997, Response filed Dec. 18, 2015 to Non Final Office Action mailed Sep. 21, 2015, 9 pgs.
U.S. Appl. No. 13/790,997, Restriction Requirement mailed Apr. 2, 2015, 8 pgs.
U.S. Appl. No. 13/833,567, Final Office Action mailed Mar. 9, 2016, 9 pgs.
U.S. Appl. No. 13/833,567, Non Final Office Action mailed Oct. 23, 2015, 10 pgs.
U.S. Appl. No. 13/833,567, Response filed Jan. 22, 2016 to Non Final Office Action mailed Oct. 23, 2015, 11 pgs.
U.S. Appl. No. 13/833,567, Response filed Jun. 25, 2015 to Restriction Requirement mailed Apr. 3, 2015, 10 pgs.
U.S. Appl. No. 13/833,567, Restriction Requirement mailed Apr. 3, 2015, 6 pgs.
U.S. Appl. No. 13/838,755, Final Office Action mailed Feb. 22, 2016, 9 pgs.
U.S. Appl. No. 13/838,755, Non Final Office Action mailed Sep. 17, 2015, 11 pgs.
U.S. Appl. No. 13/838,755, Response filed Jun. 8, 2015 to Restriction Requirement mailed Apr. 6, 2015, 1 pg.
U.S. Appl. No. 13/838,755, Response filed Dec. 1, 2015 to Non Final Office Action mailed Sep. 17, 2015, 13 pgs.
U.S. Appl. No. 13/838,755, Restriction Requirement mailed Apr. 6, 2015, 6 pgs.
U.S. Appl. No. 13/889,851, Non Final Office Action mailed Apr. 6, 2015, 10 pgs.
U.S. Appl. No. 13/889,851, Notice of Allowance mailed Aug. 12, 2015, 8 pgs.
U.S. Appl. No. 13/889,851, Response filed Feb. 26, 2015 to Restriction Requirement mailed Jan. 21, 2015, 12 pgs.
U.S. Appl. No. 13/889,851, Response filed Jul. 6, 2015 to Non Final Office Action mailed Apr. 6, 2015, 14 pgs.
U.S. Appl. No. 13/889,851, Restriction Requirement mailed Jan. 21, 2015, 6 pgs.
U.S. Appl. No. 13/889,851, Supplemental Amendment and Response filed Jul. 6, 2015 to Non Final Office Action mailed Apr. 6, 2015, 8 pgs.
U.S. Appl. No. 13/959,145, Final Office Action mailed Jan. 29, 2016, 16 pgs.
U.S. Appl. No. 13/959,145, Final Office Action mailed Feb. 5, 2015, 22 pgs.
U.S. Appl. No. 13/959,145, Non Final Office Action mailed Jul. 31, 2015, 21 pgs.
U.S. Appl. No. 13/959,145, Non Final Office Action mailed Sep. 15, 2014, 20 pgs.
U.S. Appl. No. 13/959,145, Response filed Jul. 6, 2015 to Final Office Action mailed Feb. 5, 2015, 18 pgs.
U.S. Appl. No. 13/959,145, Response filed Oct. 30, 2015 to Non Final Office Action mailed Jul. 31, 2015, 14 pgs.
U.S. Appl. No. 13/959,145, Response filed Dec. 15, 2014 to Non Final Office Action mailed Sep. 15, 2014, 21 pgs.
U.S. Appl. No. 14/055,172, Restriction Requirement mailed Mar. 4, 2016, 6 pgs.
U.S. Appl. No. 14/055,191, Restriction Requirement mailed Mar. 7, 2016, 6 pgs.
U.S. Appl. No. 14/071,295, Non Final Office Action mailed Aug. 5, 2014, 6 pgs.
U.S. Appl. No. 14/071,295, Notice of Allowance mailed Dec. 10, 2014, 8 pgs.
U.S. Appl. No. 14/071,295, Response filed Nov. 17, 2014 to Non Final Office Action mailed Aug. 15, 2014, 14 pgs.
U.S. Appl. No. 14/071,295, Supplemental Notice of Allowability mailed Jan. 26, 2015, 2 pgs.
U.S. Appl. No. 14/095,614, Preliminary Amendment filed Apr. 15, 2014, 17 pgs.
U.S. Appl. No. 14/107,350, Notice of Allowance mailed Feb. 26, 2016, 11 pgs.
U.S. Appl. No. 14/107,350, Preliminary Amendment filed Feb. 28, 2014, 4 pgs.
U.S. Appl. No. 14/211,977, Preliminary Amendment filed Mar. 2, 2016, 7 pgs.

(56) References Cited

OTHER PUBLICATIONS

U.S. Appl. No. 14/211,977, Restriction Requirement mailed Mar. 11, 2016, 6 pgs.
U.S. Appl. No. 14/275,548, Non Final Office Action mailed Feb. 19, 2016, 14 pgs.
U.S. Appl. No. 14/324,688, Non Final Office Action mailed Jan. 8, 2016, 18 pgs.
U.S. Appl. No. 14/456,286, Non Final Office Action mailed Dec. 30, 2015, 16 pgs.
U.S. Appl. No. 14/456,286, Response filed Dec. 11, 2015 to Restriction Requirement mailed Oct. 29, 2015, 6 pgs.
U.S. Appl. No. 14/456,286, Restriction Requirement mailed Oct. 29, 2015, 9 pgs.
U.S. Appl. No. 14/589,101, Final Office Action mailed Oct. 2, 2015, 10 pgs.
U.S. Appl. No. 14/589,101, Non Final Office Action mailed Feb. 12, 2015, 10 pgs.
U.S. Appl. No. 14/589,101, Response filed Jun. 12, 2015 to Non Final Office Action mailed Feb. 12, 2015, 11 pgs.
U.S. Appl. No. 14/589,101, Response filed Dec. 29, 2015 to Final Office Action mailed Oct. 2, 2015, 15 pgs.
U.S. Appl. No. 14/794,309, Preliminary Amendment filed Sep. 22, 2015, 6 pgs.
U.S. Appl. No. 14/794,309, Supplemental Preliminary Amendment filed Mar. 3, 2016, 8 pgs.
U.S. Appl. No. 14/876,167, Preliminary Amendment filed Oct. 27, 2015, 8 pgs.
U.S. Appl. No. 14/936,831, Preliminary Amendment filed Nov. 11, 2015, 6 pgs.
U.S. Appl. No. 14/956,724, Preliminary Amendment filed Dec. 7, 2015, 8 pgs.
U.S. Appl. No. 14/956,724, Supplemental Preliminary Amendment filed Feb. 11, 2016, 7 pgs.
U.S. Appl. No. 14/983,108, Preliminary Amendment filed Dec. 30, 2015, 7 pgs.
U.S. Appl. No. 14/983,747, Preliminary Amendment filed Jan. 4, 2016, 5 pgs.
U.S. Appl. No. 15/060,007, Preliminary Amendment filed Mar. 9, 2016, 9 pgs.
U.S. Appl. No. 15/061,352, Preliminary Amendment filed Mar. 7, 2016, 8 pgs.
U.S. Appl. No. 15/074,553, Preliminary Amendment filed Mar. 21, 2016, 8 pgs.
U.S. Appl. No. 12/938,902, Non Final Office Action mailed Sep. 17, 2012, 11 pgs.
U.S. Appl. No. 12/938,902, Notice of Allowance mailed Jun. 21, 2013, 13 pgs.
U.S. Appl. No. 12/938,902, Notice of Allowance mailed Oct. 1, 2013, 9 pgs.
U.S. Appl. No. 12/938,902, Response filed Aug. 6, 2012 to Restriction Requirement mailed Jul. 6, 2012, 14 pgs.
U.S. Appl. No. 12/938,902, Response filed Dec. 10, 2012 to Non Final Office Action mailed Sep. 17, 2012, 20 pgs.
U.S. Appl. No. 12/938,902, Restriction Requirement mailed Jul. 6, 2012, 8 pgs.
Bio-Intrafix Tibial Soft Tissue Fasteners, Building on the Legacy of IntraFix, (Feb. 2007), 6 pgs.
European Application Serial No. 10727548.9, Examination Notification Art. 94(3) mailed Sep. 18, 2014, 6 pgs.
European Application Serial No. 10727548.9, Office Action mailed Jan. 19, 2012, 2 pgs.
European Application Serial No. 10727548.9, Response filed Mar. 19, 2015 to Examination Notification Art. 94(3) mailed Sep. 18, 2014, 23 pgs.
European Application Serial No. 11707316.3, Examination Notification Art. 94(3) mailed Feb. 4, 2014, 3 pgs.
European Application Serial No. 11707316.3, Examination Notification Art. 94(3) mailed Dec. 17, 2014, 5 pgs.
European Application Serial No. 11707316.3, Office Action mailed Nov. 10, 2015, 6 pgs.
European Application Serial No. 11707316.3, Response filed Jun. 5, 2014 to Examination Notification Art. 94(3) mailed Feb. 4, 2014, 7 pgs.
European Application Serial No. 11707316.3, Response filed Jun. 29, 2015 to Examination Notification Art. 94(3) mailed Dec. 17, 2014, 25 pgs.
European Application Serial No. 12721676.0, Office Action mailed Jan. 3, 2014, 2 pgs.
European Application Serial No. 12721676.0, Preliminary Amendment filed Nov. 19, 2013, 9 pgs.
European Application Serial No. 12721676.0, Response filed Jul. 10, 2014 to Office Action mailed Jan. 3, 2014, 2 pgs.
European Application Serial No. 12791902.5, Examination Notification Art. 94(3) mailed Aug. 14, 2015, 4 pgs.
European Application Serial No. 12791902.5, Office Action mailed Jul. 15, 2014, 2 pgs.
European Application Serial No. 12806211.4, Examination Notification Art. 94(3) mailed Aug. 13, 2015, 5 pgs.
European Application Serial No. 12806211.4, Office Action mailed Jul. 18, 2014, 2 pgs.
European Application Serial No. 13818131.8, Office Action mailed Jul. 28, 2015, 2 pgs.
European Application Serial No. 13818131.8, Response filed Feb. 8, 2016 to Office Action mailed Jul. 28, 2015, 14 pgs.
European Application Serial No. 14716173.1, Office Action mailed Nov. 5, 2015, 2 pgs.
International Application Serial No. PCT/US2009/039580, International Preliminary Report on Patentability mailed Nov. 4, 2010, 9 pgs.
International Application Serial No. PCT/US2009/039580, International Search Report mailed Jul. 30, 2009, 4 pgs.
International Application Serial No. PCT/US2009/039580, Written Opinion mailed Jul. 30, 2009, 7 pgs.
International Application Serial No. PCT/US2010/036602, International Preliminary Report on Patentability mailed Dec. 8, 2011, 9 pgs.
International Application Serial No. PCT/US2010/036602, International Search Report mailed Nov. 8, 2010, 6 pgs.
International Application Serial No. PCT/US2010/036602, Written Opinion mailed Nov. 8, 2010, 7 pgs.
International Application Serial No. PCT/US2012/030294, International Preliminary Report on Patentability mailed Oct. 10, 2013, 9 pgs.
International Application Serial No. PCT/US2012/030294, International Search Report mailed May 23, 2012, 6 pgs.
International Application Serial No. PCT/US2012/030294, Written Opinion mailed May 23, 2012, 7 pgs.
International Application Serial No. PCT/US2012/037703, Written Opinion mailed Nov. 28, 2013.
International Application Serial No. PCT/US2012/062738, International Preliminary Report on Patentability mailed May 15, 2014, 9 pgs.
International Application Serial No. PCT/US2012/062738, International Search Report mailed Mar. 6, 2013, 6 pgs.
International Application Serial No. PCT/US2012/062738, Written Opinion mailed Mar. 6, 2013, 7 pgs.
International Application Serial No. PCT/US2013/075989, International Preliminary Report on Patentability mailed Jul. 2, 2015, 10 pgs.
International Application Serial No. PCT/US2014/026413, International Preliminary Report on Patentability mailed Sep. 24, 2015, 10 pgs.
"Mallory-Head Modular Calcar Revision System", Biomet Orthopedics, Inc., (2006), 1-16.
"SportMesh™ Soft Tissue Reinforcment, Made from . . . Artelon® optimal tissue repair", Biomet® Sports Medicine, Inc., (2007), 8 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Anitua, Eduardo, et al., "Autologous platelets as a source of proteins for healing and tissue regeneration", Thromb Haemost, vol. 91, (2004), 4-15.

(56) References Cited

OTHER PUBLICATIONS

Edwards, Andrew, et al., "The Attachments of the Fiber Bundles of the Posterior Cruciate ligament: an Anatomic Study", Arthroscopy: The Journal of Arthroscopic and Related Surgery, vol. 23, No. 3, (Mar. 2008), 284-290.

Floryan, K, et al., "Intraoperative use of Autologous Platelet-Rich and Platelet-Poor Plasma for Orthopedic Surgery Patients", AORN Journal: Home Study Program, 80(4), (Oct. 2004), 667-674.

Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.

Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.

Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.

Roseberg, MD, Thomas D, "ACL Reconstruction with Acufex Director Drill Guide and Endobutton CL Fixation System", Smith & Nephew: Knee Series, Technique Guide, (2005), 12 pgs.

Steadman, et al., "Microfracture: Surgical Technique and Rehabilitation to Treat Chondral Defects", Clinical Orthopaedics and Related Research 391, (2001), S362-S369.

* cited by examiner

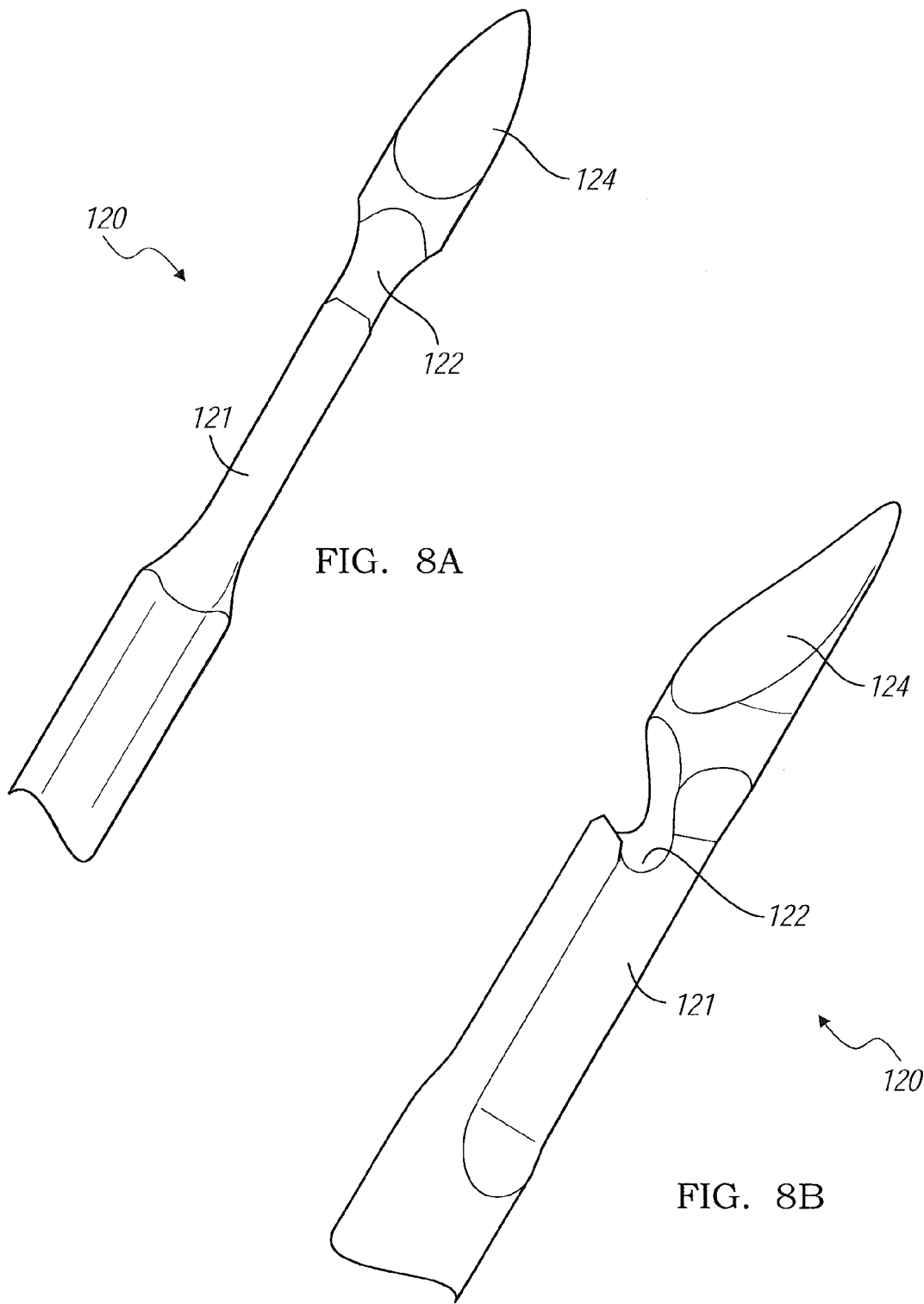

SOFT TISSUE REPAIR ASSEMBLY AND ASSOCIATED METHOD

CROSS-REFERENCE TO RELATED APPLICATIONS

This application is a continuation of U.S. patent application Ser. No. 12/828,977 filed Jul. 1, 2010, now U.S. Pat. No. 8,409,253 issued on Apr. 2, 2013, which is a divisional of U.S. patent application Ser. No. 11/347,661 filed on Feb. 3, 2006, now U.S. Pat. No. 7,749,250 issued on Jul. 6, 2010. The entire disclosure of the above application is incorporated herein by reference.

INTRODUCTION

Tears caused by trauma or disease in soft tissue, such as cartilage, ligament, or muscle, can be repaired by suturing. Various assemblies have been developed for facilitating suturing and are effective for their intended purposes. Nevertheless, tissue repair assemblies for facilitating suturing are still desirable.

SUMMARY

The present teachings provide a soft tissue repair assembly. The assembly includes a flexible member having first and second ends, and a flexible strand passing through the flexible member. The strand has first and second strand ends extending through the flexible member, such that pulling at least one of the first and second strand ends changes the flexible member from a first shape suitable for insertion through soft tissue to a second shape suitable for securely lodging the soft tissue repair assembly relative to soft tissue.

The present teachings provide a soft tissue repair assembly that includes an inserter, at least one flexible member preloaded on the inserter in a first shape, and a flexible strand coupled to the flexible member for changing the shape of the flexible member from the first shape to a second shape after implantation, wherein the second shape is suitable for securely lodging the flexible member relative to soft tissue.

The present teachings provide a method for repairing a tear in soft tissue. The method includes preloading a flexible member coupled to a flexible strand on an inserter, inserting the inserter through tissue from a first side of the tear to a second side of the tear, and deploying the flexible member relative to the soft tissue. The method further includes tensioning the strand, changing the shape of the flexible member from a first shape to a second shape suitable for securely lodging the flexible member relative to the soft tissue, and reducing or closing the tear.

The present teachings provide a method for repairing a tear in a meniscus during arthroscopic knee procedure. The method includes inserting an inserter through the tear to an outer surface of the meniscus, deploying a first flexible member coupled to a flexible strand from the inserter on an outer surface of the meniscus, tensioning the strand, changing the shape of the first flexible member from a first shape to a second shape for securing the flexible member on the outer surface, and reducing or closing the tear.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 8A is a plan view of an inserter according to the present teachings;

FIG. 8B is a side view of the inserter of FIG. 8A;

DESCRIPTION OF VARIOUS ASPECTS

The following description is merely exemplary in nature and is in no way intended to limit the invention, its application, or uses. For example, although the present teachings are illustrated in an application for meniscus repair in knee surgery, the present teachings can also be used for repairing any tissue, such as bone, muscle, ligament or tendon in an arthroscopic or other open procedure.

Figure 1:
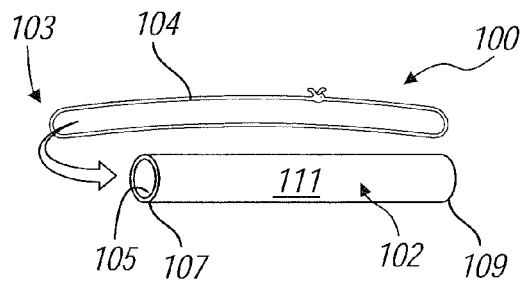
FIG. 1 is an exploded view of a soft-tissue repair assembly according to the present teachings.
Figure 7A:
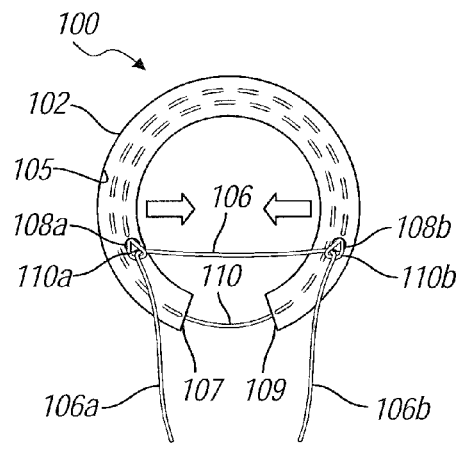
FIG. 7A is a plan view of a soft-tissue repair assembly according to the present teachings, shown in a first shape.
Figure 7B:
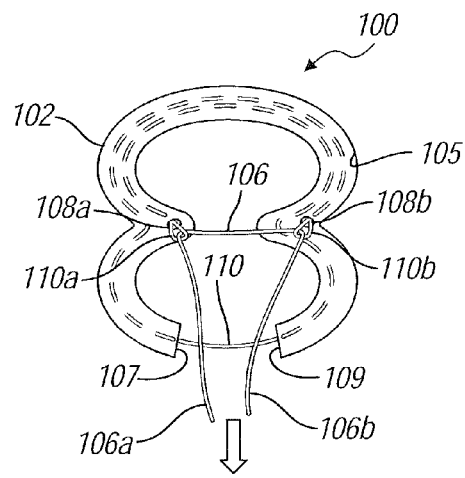
FIG. 7B is a plan view of the soft-tissue repair assembly of FIG. 7A, shown in a second shape.
Figure 7C:
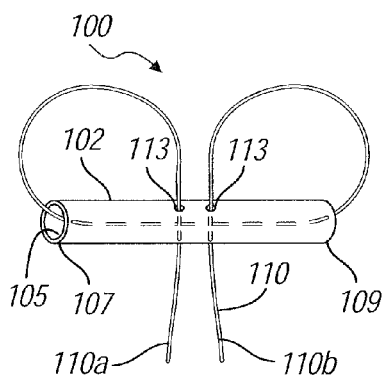
FIG. 7C is a plan view of a soft-tissue repair assembly according to the present teachings, shown in a first shape.
Figure 7D:
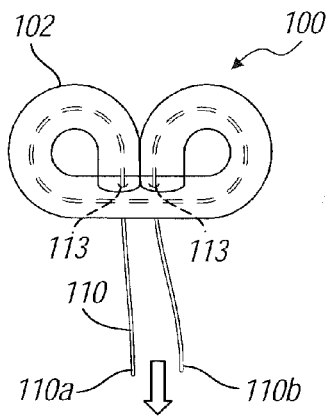
FIG. 7D is a plan view of the soft-tissue repair assembly of FIG. 7C, shown in a second shape.
Figure 7E:
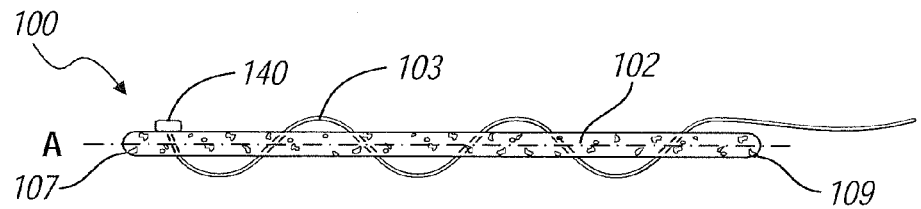
FIG. 7E is a plan view of a soft-tissue repair assembly according to the present teachings, shown in a first shape.

Referring to FIG. 1 and FIG. 7E, an exemplary soft tissue repair assembly 100 according to the present teachings can include a flexible member 102, and a flexible strand 103, such as, for example, thread, ligament, wire, or suture. The strand 103 can be coupled with the flexible member 102 for changing the shape of the flexible member 102. The flexible member 102 can be an elongated member having first and second ends 107, 109. The elongated member can include a substantially cylindrical wall 111 having a longitudinal bore 105, as illustrated in FIG. 1, or can be a flexible elongated solid member 102 with a bore, as illustrated in FIG. 7E, or any other shape. The flexible member 102 can be made of resorbable or non-resorbable materials, including sponges and sponge-like materials in solid form, perforated materials, woven/braided from biocompatible materials or fibers, such as, for example, polymer, polyester, polyethylene, cotton, silk, or other natural or synthetic materials, include sponges and sponge-like materials. The flexible member 102 can also be an elongated tubular or solid member or a two-dimensional member with or without internal bores. The flexible member 102 can have any properties that allow the flexible member 102 to change shape. The flexible member 102 can be, for example, compliant, flexible, foldable, squashable, squeezable, deformable, limp, flaccid, elastic, low-modulus, soft, spongy, perforated or any other flexible member which can change shape. In some aspects, the flexible member 102 can be coated with biological or biocompatible coatings, and it can also be soaked in platelets and other biologics, which can be easily absorbed by the flexible member 102 in particular when, for example, the flexible member 102 is made from spongy, absorbent material.

Referring to FIGS. 1-4, the flexible strand 103 can include an inner loop portion 104 and outer strand portion 106. The inner loop portion 104 can be substantially contained within the bore 105, such that the inner loop portion 104 extends from the first end 107 of the bore 105, passes through the bore 105, and terminates at the second end 109 of the bore 105. The outer strand portion 106 can be coupled to the loop portion 104 adjacent the first and second ends 107, 109 and can extend substantially outside the flexible member 102.

Figure 3:
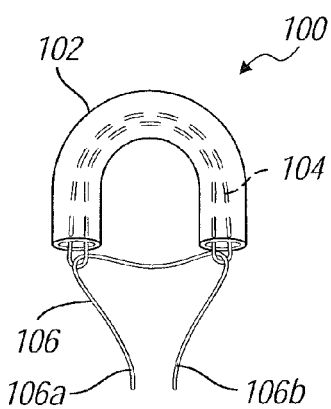
FIG. 3 is a perspective view of the soft-tissue repair assembly of FIG. 2, shown in a second shape.
Figure 2:
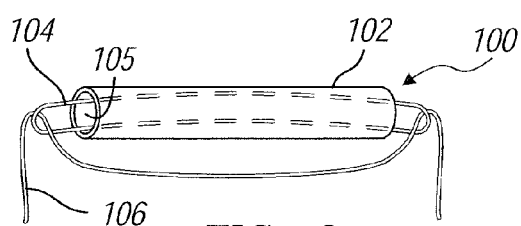
FIG. 2 is a perspective view of a soft-tissue repair assembly according to the present teachings, shown in a first shape.
Figure 4:
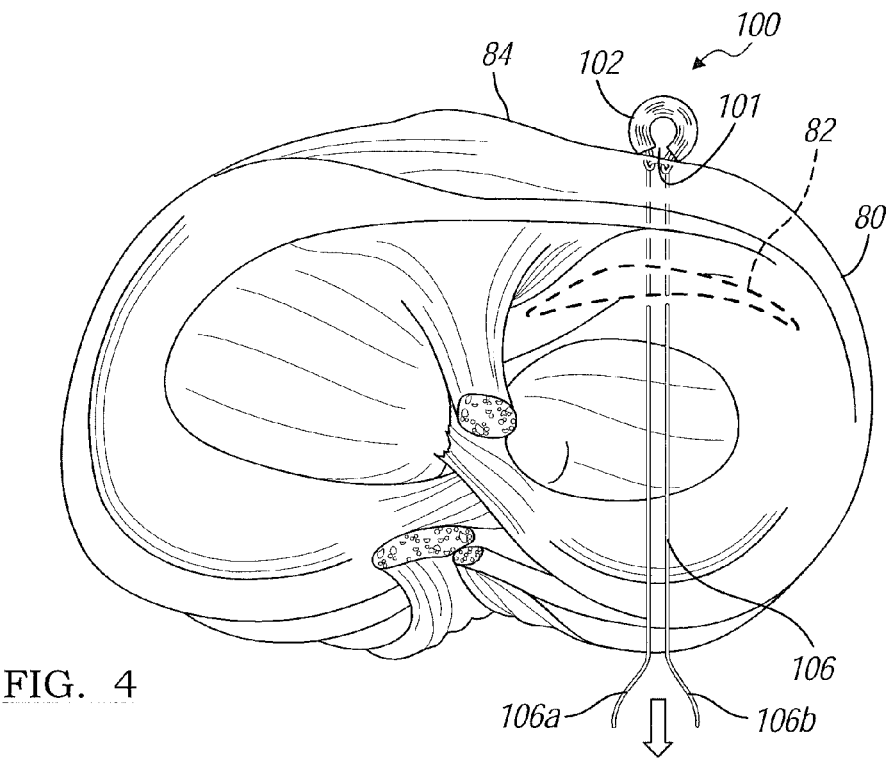
FIG. 4 is an environmental view of the soft-tissue repair assembly of FIG. 2, shown implanted relative to soft tissue.

The strand 103 can be made of braided filaments or fibers of biocompatible material, including natural and synthetic fibers, such as cotton, silk, polymer, polyester, polyethylene, and other materials. The inner loop portion 104 can be knotted, as shown in FIG. 1, or continuous, as shown in FIG. 2. The outer strand portion 106 can be a separate piece of strand 103 and can include first and second ends 106a, 106b. Pulling at the ends 106a, 106b, or at least one of the ends 106a, 106b while holding the other end fixed, when the flexible member 102 is implanted relative to soft tissue or on an outer surface of soft tissue causes the flexible member 102 to change shape from a first shape to a second or implanted shape. The first shape of the flexible member 102 can be a thin elongated shape with length to width (aspect ratio) greater than one. The first shape of the flexible member 102 can also be a folded shape. The implanted shape of the flexible member 102 can be a bulkier shape with length to width ratio close to one, as illustrated in FIGS. 3 and 4, for snugly securing the flexible member 102 relative to or on an outer surface of soft tissue 80. The implanted shape of the flexible member 102 can have bigger overall width or enclosed cross-sectional area or volume than those of the first shape such that the flexible member 102 cannot be pulled out of the same opening through which it was originally inserted. In one aspect, the flexible member 102 can retain its bulkier shape after implantation, even after the tension on the strand portion 106 is removed.

Figure 5:
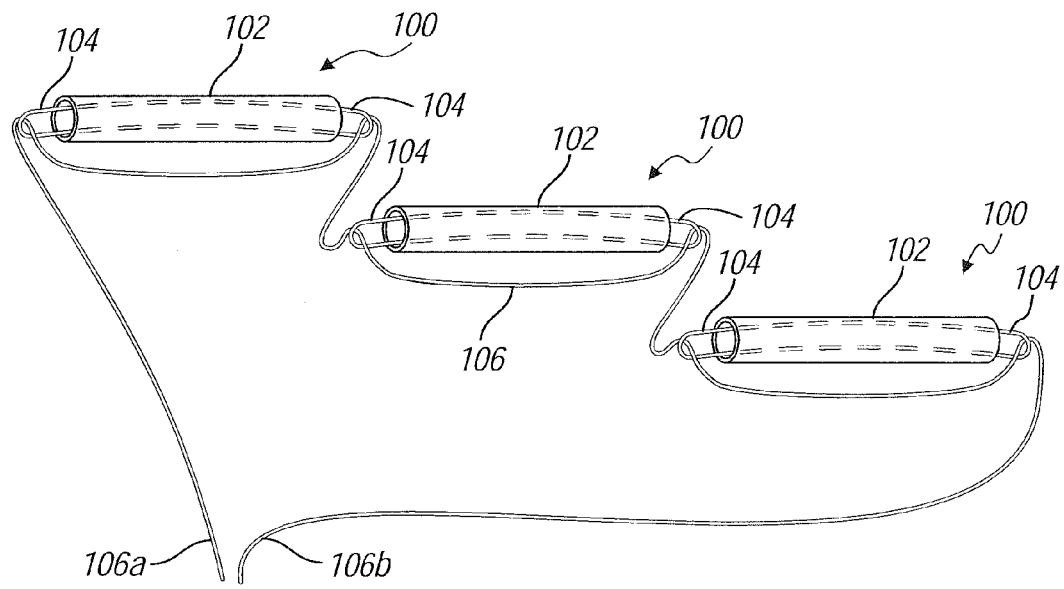
FIG. 5 is a perspective view of a plurality of connected soft-tissue repair assemblies according to the present teachings shown in first shapes.
Figure 6:
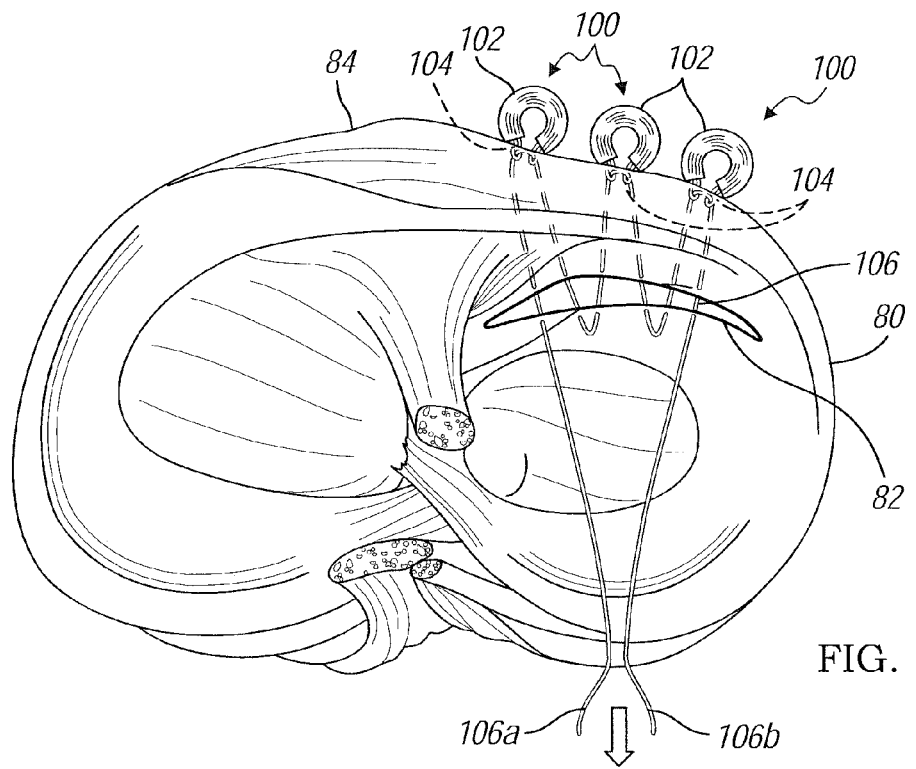
FIG. 6 is an environmental view of the soft-tissue repair assemblies of FIG. 5, shown in second shapes and implanted relative to soft tissue.

In the exemplary illustration of FIG. 4, the soft-tissue repair assembly 100 is shown implanted on an outer surface 84, such as a posterior surface of a meniscal soft tissue 80, after passing through a tear 82 for reducing or closing the tear 82. In FIG. 4, the suture securing second shape of the flexible member 102 is substantially a circular shape, but having a slit or gap 101. Referring to FIGS. 5 and 6, multiple soft tissue repair assemblies 100 can be daisy-chained together by a single continuous outer strand portion 106 connected to each inner loop portion 104 for reducing the tear 82. Generally, the soft-tissue repair assembly 100 can be positioned relative to soft tissue, such as in the soft tissue, adjacent the soft tissue, or on an outer surface of the soft tissue.

Referring to FIG. 7A, a continuous strand 110 can be used to define an inner loop having an outer portion and loop ends 110a, 110b. After the strand 110 is looped around the bore 105 of the flexible member 102, such that the first and second ends 107, 109 of the flexible member 102 are coupled by the outer portion of the strand 110, the loop ends 110a, 110b of the continuous strand 110 exit the bore 105 through small wall openings 108a, 108b adjacent but displaced from the ends 107, 109 of the flexible member 102. A second strand 106 having ends 106a, 106b is looped around the loop ends 110a, 110b. Pulling the ends 106a, 106b, of the second strand 106 causes the flexible member 102 to change shape to an eight-like securing shape, which appears pinched in the vicinity of the openings 108a, 108b, as illustrated in FIG. 7B. The eight-like shape of the flexible member 102 provides a geometry that encloses bigger area or volume for the same length of flexible member. Bigger securing volume can prevent the flexible member 102 from being pulled out of the insertion opening, and can provide secure and strong anchoring in various applications at the discretion of the surgeon.

Referring to FIGS. 7C and 7D, a continuous strand 110 can be passed through the bore 105 of the flexible member 102, such the strand ends 110a, 110b exit through wall openings 113 defined away from the flexible member ends 107, 109, in a middle section of the flexible member 102, such that pulling the strand ends 110a, 110b away from the flexible member 102, causes the flexible member 102 to change shape into a pretzel-like securing shape, which can be selected for application when bigger enclosed area/volume is desired for the same length of flexible member 102. It will be appreciated that the wall openings 113, as well as the wall openings 108a, 108b discussed above in connection with FIGS. 7A, 7B, do not need to be preformed holes. The wall openings 113, 108a, 108b, can be for example, space between fibers when the flexible member is woven or braided. The strand 110 can be passed through the wall 111 or between woven/braided fibers of the flexible member 102 using a suture threader, for example, or other instrument. The wall openings 108a, 108b and 113 can allow the flexible member 102 to slide relatively freely along at least a portion of the strand 110, thereby helping to position the strand 110 before changing the shape of the flexible member 102 to the final implantation and suture securing shape.

It will be appreciated that various soft-tissue suture securing shapes, including those described above as well as other shapes, can be used with the same flexible member 102 by varying the manner of looping the strand or strand portions or separate strands relative to the flexible member 102, and varying the number and/or location of various openings, such as the openings 108a, 108b, 113 described above, for producing a desired suture-securing shape. Generally, the suture-securing shapes have a bulky shape and occupy a greater volume for securing the flexible member 102 snuggly into soft tissue. Furthermore, the flexible member 102 lacks any sharp or cutting elements, sharp points, edges, or planes, such as barbs, hooks, fins, pins, threads, ribs, or other tissue-piercing features, generally associated sharp-element anchoring. Accordingly, the soft tissue repair assembly 102, in its various shapes, does not pierce or cut or otherwise injure soft tissue, and does not rely on sharp-element anchoring for securing suture into soft tissue. On the contrary, the soft-tissue repair assembly 100 provides suture securing that can be effected by changing the shape of the flexible member 102 into a bulkier second shape, which is relatively smooth and lacks any sharp elements or geometric features. In the bulkier shape the flexible member 102 can be lodged tightly outside soft tissue, or in or between layers of soft tissue, possibly displacing soft tissue, but without piercing, cutting or otherwise damaging soft tissue. In the bulkier shape, the flexible member 102 can be prevented from backing out of the original insertion opening, or tearing through tissue.

Figure 7F:
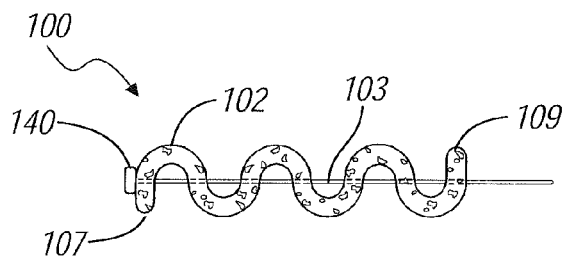
FIG. 7F is a plan view of the soft-tissue repair assembly of FIG. 7A, shown in a second shape.
Figure 7G:
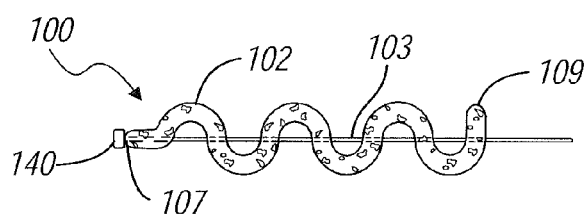
FIG. 7G is a plan view of a soft-tissue repair assembly according to the present teachings.

Referring to FIGS. 7E-7G, the elongated flexible member 102 can be coupled with a flexible strand 103 which can be retained with a button or knot or other retainer 140 adjacent a first end 107 of the flexible member 102 and then threaded in and out of the flexible member 102 along a longitudinal axis A of the flexible member 102 exiting adjacent a second end 109 of the flexible member 102. Pulling the strand 103 away from the retainer 140 can cause the flexible member 102 to scrunch up against the retainer 140 in a wavy, zigzag, multi-fold or accordion-like fashion, as illustrated in FIGS. 7F and 7G. The flexile member 102 can have a solid or annular cross-section.

Figure 7H:
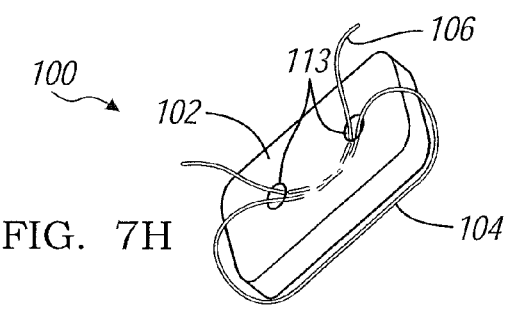
FIG. 7H is a plan view of a soft-tissue repair assembly according to the present teachings, shown in a first shape.
Figure 7I:
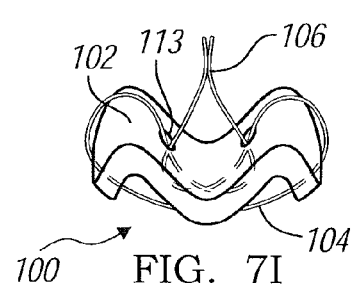
FIG. 7I is a plan view of the soft-tissue repair assembly of FIG. 7H, shown in a second shape.
Figure 7J:
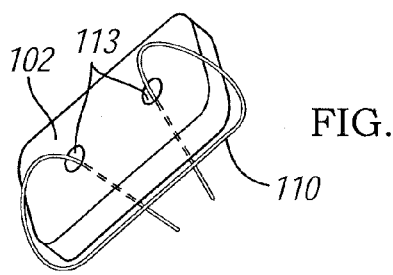
FIG. 7J is a plan view of a soft-tissue repair assembly according to the present teachings.
Figure 7K:
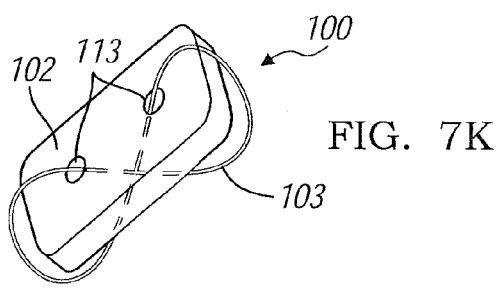
FIG. 7K is a plan view of a soft-tissue repair assembly according to the present teachings.
Figure 9A:
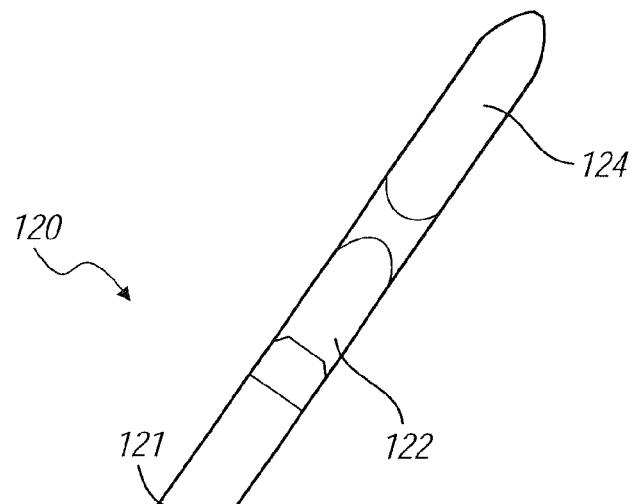
FIG. 9A is a plan view of an inserter according to the present teachings.
Figure 9B:
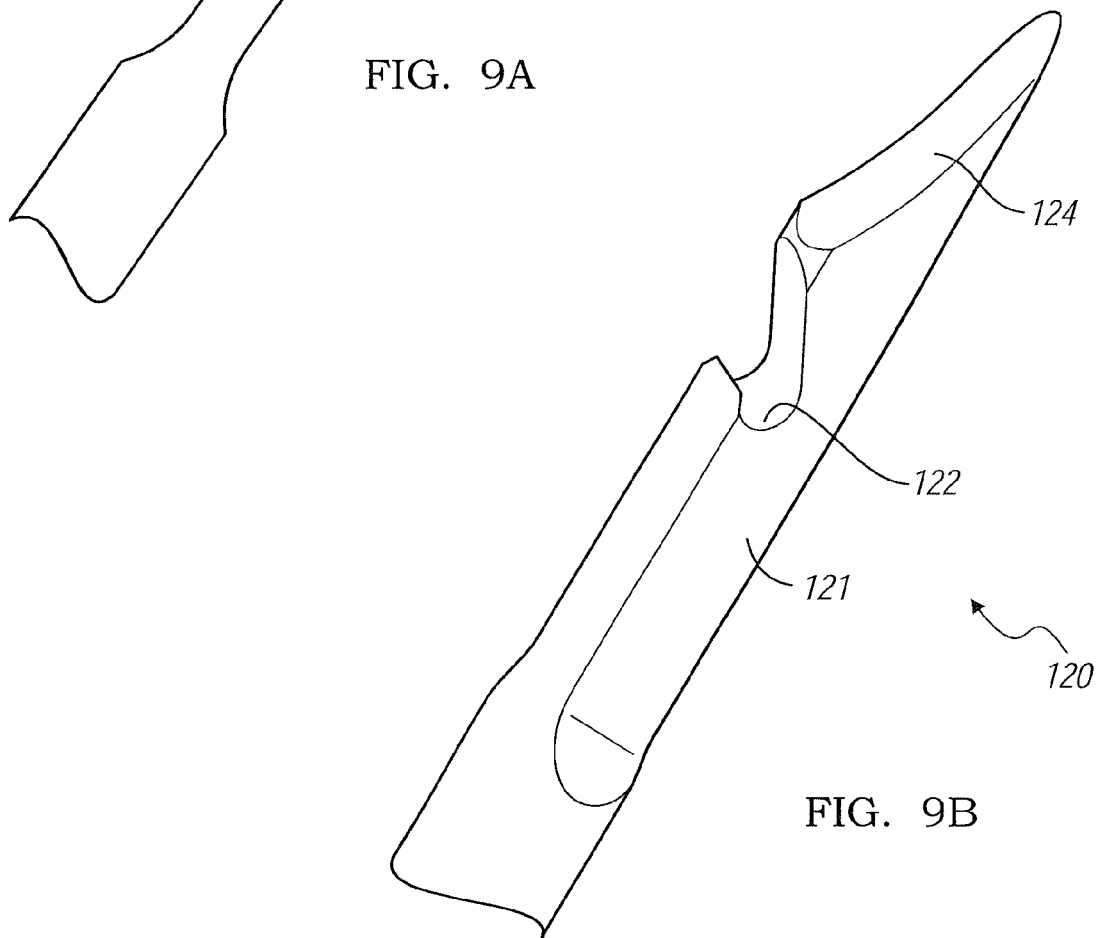
FIG. 9B is a side view of the inserter of FIG. 9A.

Referring to FIGS. 7H-7K, the flexible member 102 can have a substantially flat, planar or generally two-dimensional shape, formed, for example, as a flat sponge or a piece of woven fabric or other flaccid material which can be pierced for passing a single strand 110 therethrough, as illustrated in FIG. 7J, or for passing a strand loop 104 coupled with an open strand 106, as illustrated in FIG. 7H. A piece of strand 103 can be passed through the flexible member 102 in various other configurations, including, for example, the configuration illustrated in FIG. 9K. Pulling at least one the strand 103, 106, 110 can cause the flexible member 102 to change shape. FIG. 7I, for example, illustrates the new shape of the flexible member 102 of FIG. 7H, after tensioning the strand 106.

Figure 14:
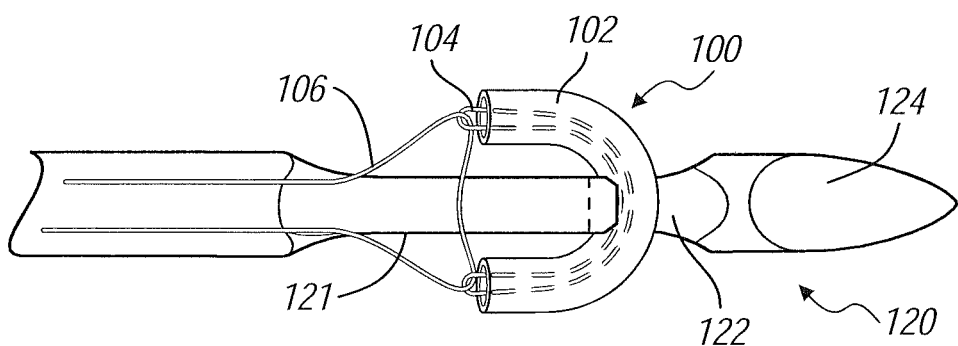
FIG. 14 is a plan view of an inserter shown holding a soft-tissue repair assembly according to the present teachings.
Figure 15:
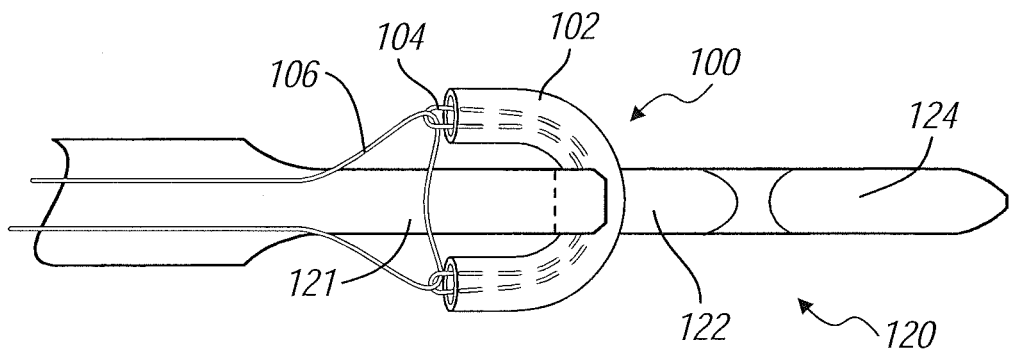
FIG. 15 is a plan view of an inserter shown holding a soft-tissue repair assembly according to the present teachings.

Referring to FIGS. 8A-15, various instruments can be used for implanting one or more soft tissue assemblies 100 relative to soft tissue. FIGS. 8A, 8B and 14 illustrate an inserter 120 having a rounded angled tip surface 124 and a shaft 121 defining a cutout or groove 122. The groove 122 can be configured for supporting a single flexible member 102 in a bent or folded shape draped over the groove 122, as illustrated in FIG. 14. FIGS. 9A, 9B and 15, illustrate a similar inserter 120 having a substantially rectangular angled tip surface 124. A sleeve 125 can be placed over the flexible member 102 to protect and keep the flexible member 102 and the strand 106 on the inserter 120, as illustrated in FIG. 15.

Figure 10:
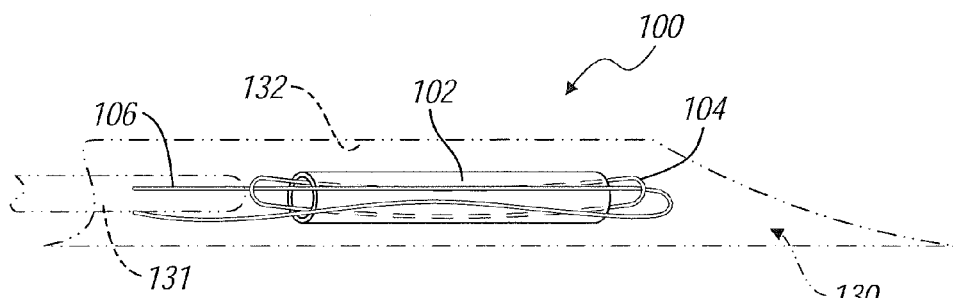
FIG. 10 is a side view of an inserter shown holding a soft-tissue repair assembly according to the present teachings.
Figure 10A:
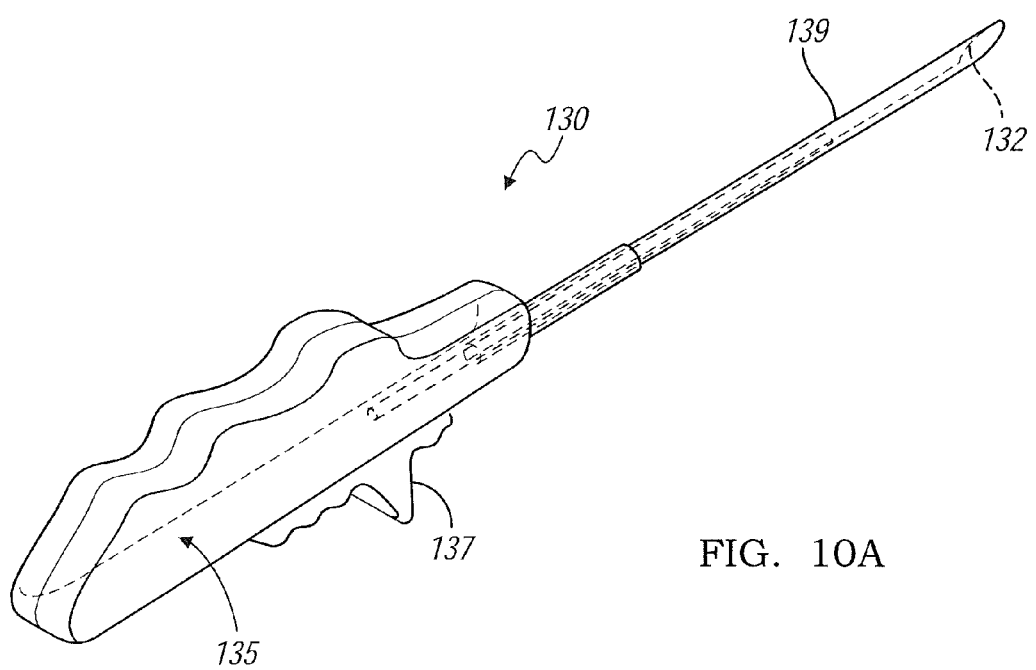
FIG. 10A is a perspective view of an exemplary inserter, according to the present teachings.
Figure 11:
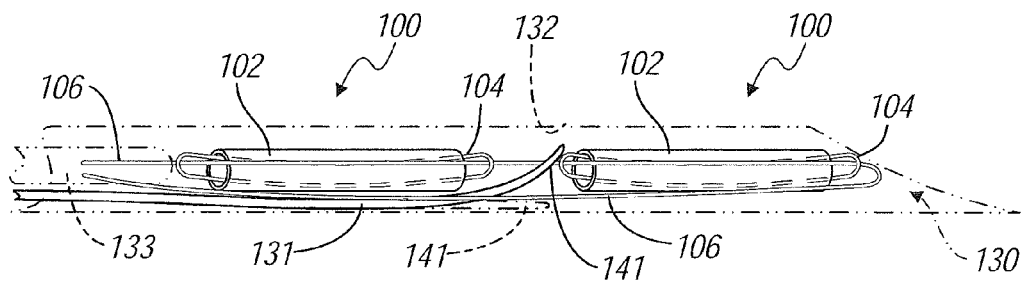
FIG. 11 is a side view of an inserter shown holding two soft-tissue repair assemblies according to the present teachings.
Figure 11A:
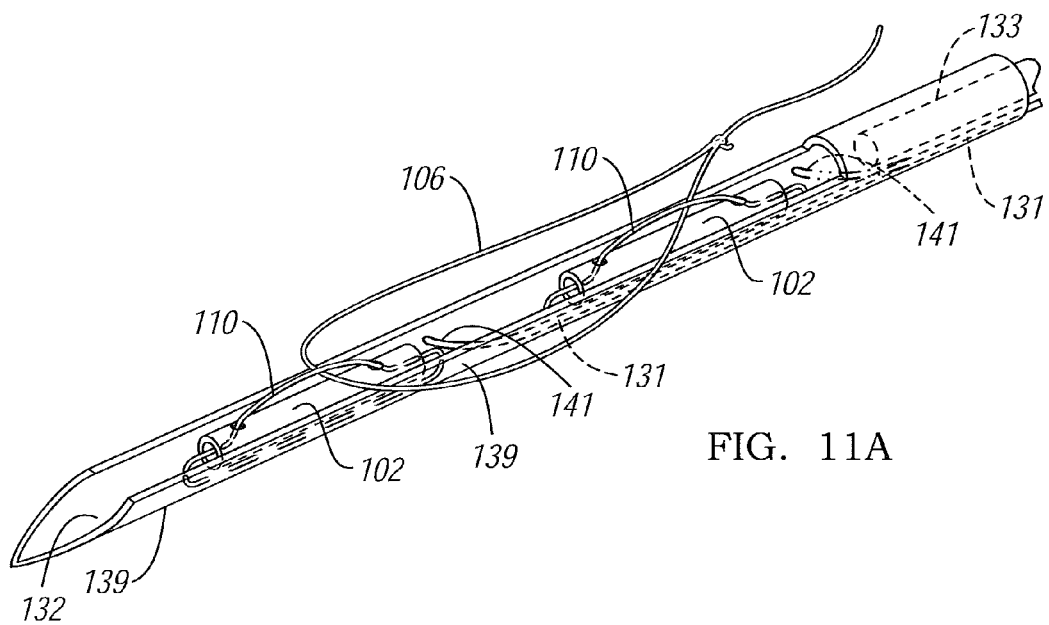
FIG. 11A is a side view of an inserter shown holding two soft-tissue repair assemblies according to the present teachings.
Figure 12:
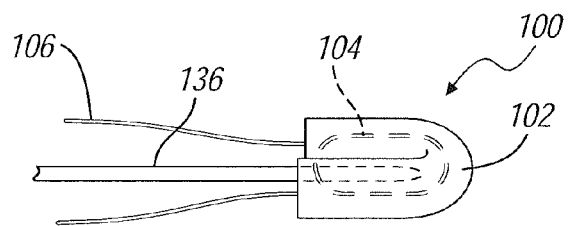
FIG. 12 is a side view of an inserter shown holding a soft-tissue repair assembly according to the present teachings.
Figure 13:
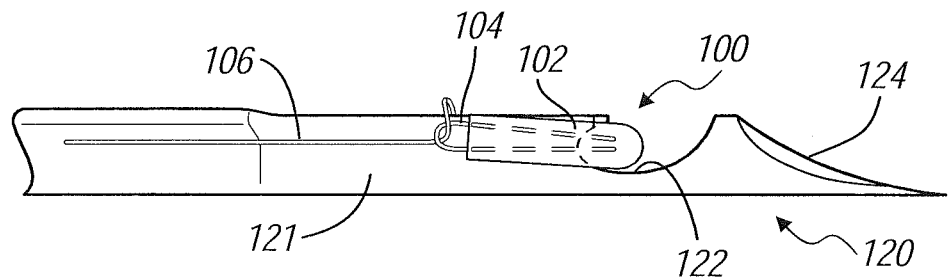
FIG. 13 is a side view of an inserter shown holding a soft-tissue repair assembly according to the present teachings.

Referring to FIGS. 10, 10A, 11 and 11A, one or more soft tissue assemblies 100 can be preloaded in a tubular inserter 130, such as the exemplary inserter 130 illustrated in FIG. 10A. The inserter 130 can include a handle 145 with a slider 137 and a shaft carrying a needle 139 having a bore 132. The flexible members 102 of the soft tissue assemblies 100 can be pushed out of the bore 132 using a plunger, a flexible pusher, such as a nitinol pusher, or other similar tool 131 operated by the slider 137. Referring to FIG. 11A, in an exemplary aspect two flexible members 102 are shown preloaded in the bore 132 of the needle 139 ahead of a stop 133. The flexible members 102 can be coupled by a strand 106 with a pre-knotted slip knot as discussed above, and can be separated by a curved end 141 of the flexible pusher 131. The curved end 141 of the flexible pusher 131 can push the first flexible member 102 out of the needle 139. The curved end 141 of the flexible pusher 131 can be straightened out as the flexible pusher 131 is retracted under the second flexible member 102, and positioned ahead of the stop 133 for pushing the second flexible member 102 out of the needle 139. Referring to FIG. 12, in another aspect, a single soft tissue assembly 100 can be loaded on a fork of a forked inserter 136.

In an exemplary soft tissue repair procedure, such as repair of a meniscal tear 82, one of the inserters 120, 130, 136, pre-loaded with at least one soft tissue repair assembly 100, can be inserted through a knee incision and through the meniscal tear 82. The flexible member 102 with the strand 106 coupled thereto can be implanted past the tear 82 on the posterior or outer surface 84 of the meniscal soft tissue 80, as illustrated, for example, in FIG. 4. The inserter 120, 130, 136 can then be removed leaving the strand ends 106a, 106b extending through the tear 82. Pulling the strand ends 106a, 106b away from the tear 82, causes the flexible member 102 to change shape into a suture securing shape, as discussed above, securely lodged on the outer surface soft tissue, without piercing, cutting or otherwise damaging tissue. The pulling action of the strand 106 reduces or closes the opening of the tear 82. Multiple soft-tissue repair assemblies 100 can be similarly implanted in daisy-chain fashion, as illustrated in FIG. 6, using the tubular inserter 130 with the multiple repair assemblies pre-loaded therein, or one by one, disconnectedly. Similar implanting procedures can be used for the soft-tissue repair assemblies 100 illustrated in FIGS. 7A, 7C, 7E, 7G, 7H, 7I and 7K. After implantation, the strand ends 106a, 106b or 110a, 110b can be secured with a knot, such as, for example, a pre-tied, self-locking slip knot, or other knot, and optionally with the help of a retainer, such as a retaining button, anchor, or other auxiliary retaining device (not shown).

During insertion and before implantation, the flexible member 102 can be supported and maintained in the bore 132 of the tubular inserter 130 in a linear shape, as illustrated in FIGS. 10, 11 and 11A. After deployment from the tubular inserter 130 for implantation relative to tissue, the flexible member 102 can change shape from a first shape into a second securing shape of curvilinear profile by tensioning the strand 106. In another aspect, the flexible member 102 can be supported or draped on the grooved inserter 120 or on the forked inserter 136 in a substantially folded or U-shape, as illustrated in FIGS. 14, 15 and 12. After deployment from the grooved inserter 120 or the forked inserter 136 for implantation relative to tissue, the flexible member 102 can be changed into a securing shape of curvilinear profile by tensioning the strand 106, as described above. It is noted that the substantially folded or U-shape, which is used with the grooved inserter 120 or the forked inserter 136 for loading the flexible member 102, is an intermediate shape between the first linear shape, and the securing shape of curvilinear profile that provides a bulky shape for securely lodging the flexible member 102 into tissue.

In another aspect, and referring to FIGS. 16-20, a soft-tissue repair assembly 100 can include one or more linear pipettes or pipette segments 150 over a strand 154 that can be used to reduce or close the tear 82. The repair-promoting pipette 150 can be made of resorbable or non-resorbable polymeric materials, collagen, allograft, such as segments of arteries or veins, or other solid-wall or woven/braided porous materials. The pipette 150 can also include perforations 162 for promoting additional biological flow. The strand 154 can pass through the tear 82 for reducing the opening of the tear 82, and can be secured with a knot 156. The soft-tissue repair assembly 100 can include one or more soft-tissue repair-promoting small tubes or pipettes 150, which can create conduits for vascularization and/or flow of nutrients, blood and other biological fluids and substances.

Figure 16:
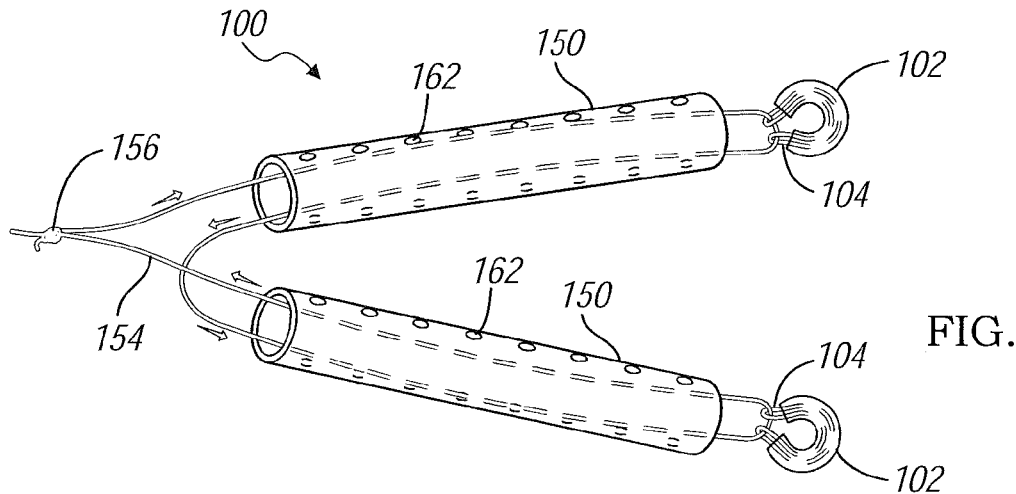
FIG. 16 is a perspective view of a soft-tissue repair assembly according to the present teachings.

Referring to FIG. 16, for example, the strand 154 can enter and pass through a first pipette 150 in one direction, pass through strand loop 104 of a first flexible member 102, pass through the first pipette 150 in the opposite direction and exit the first pipette 150, and similarly pass through the second pipette 150, the second flexible member 102, and out of the second pipette 150, as illustrated by the directional arrows along the strand 154.

Figure 17:
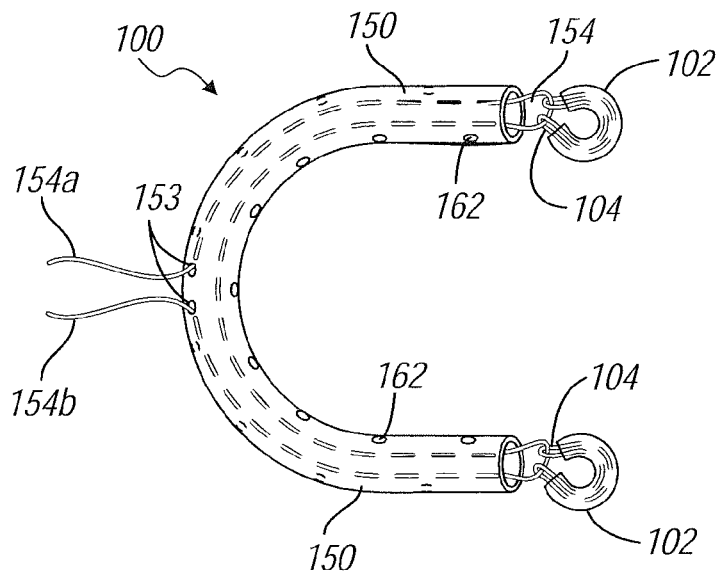
FIG. 17 is a perspective view of a soft-tissue repair assembly according to the present teachings.

Referring to FIG. 17, a single U-shaped pipette 150 can be used to run along the strand 154 between two flexible members 102. The strand ends 154a, 154b can exit the pipette 152 through small openings 153 at the bottom of the "U". The U-shape can be provided by using an originally straight, but flexible/compliant pipette 150 that changes shape while following the U-shaped portion of the strand 154 between the two flexible members 102, or by providing an originally curved pipette 150.

Figure 18:
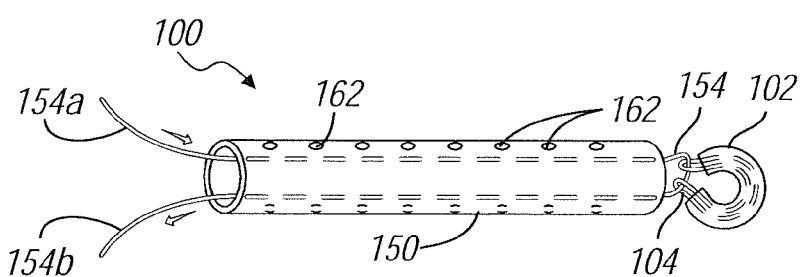
FIG. 18 is a perspective view of a soft-tissue repair assembly according to the present teachings.
Figure 19:
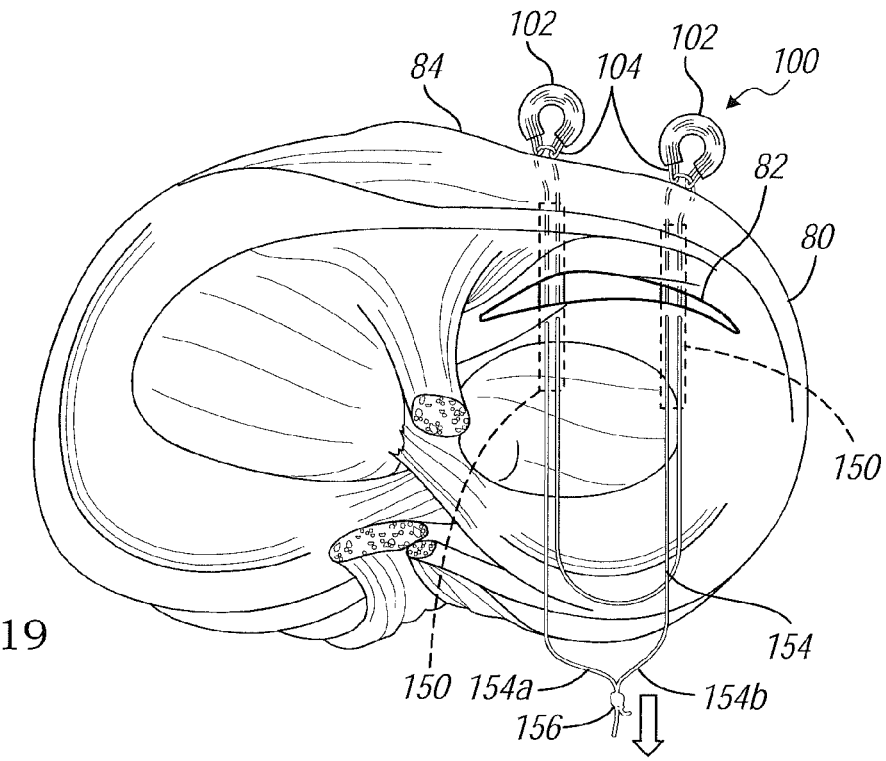
FIG. 19 is an environmental view of a soft-tissue repair assembly according to the present teachings.
Figure 20:
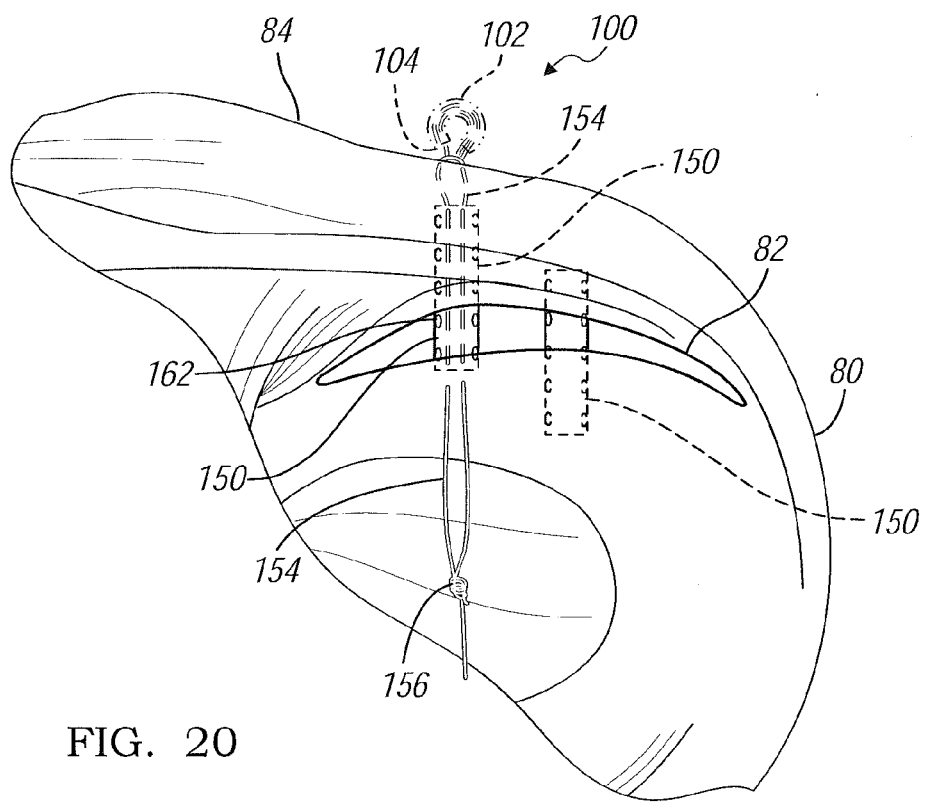
FIG. 20 is an environmental view of a soft-tissue repair assembly according to the present teachings.

Referring to FIGS. 18 and 20, a single pipette 150 can be used with one flexible member 102, with the strand 154 entering and exiting the pipette 150 in opposite directions before and after passing through the suture loop 104 of the flexible member 102. The flexible member 102 can be optionally used, or can be omitted entirely, as indicated by phantom lines in FIG. 20. Referring to FIG. 19, two pipettes 150 can be used over corresponding portions of the suture 154, with or without the use of flexible members 102. Additionally, one or more pipettes 150 can be used independently without any suture or strand 154 passing therethrough for promoting vascularization and healing.

Referring to FIGS. 4 and 6, the tissue repair assembly 100 can be used, for example, for implanting one flexible member 102, or multiple flexible members 102 for meniscal repair in an arthroscopic knee procedure. Referring to FIG. 4 an exemplary repair using a single flexible member 102 is illustrated. The flexible member 102 can be implanted using one of the inserters 120, 130, 136 discussed above and illustrated in FIGS. 8-15. The inserter 120, 130, 136 can inserted, with the flexible member 102 pre-loaded in a first shape, as discussed above, into meniscal tissue 80 through the meniscal tear 82. The flexible member 102 can be deployed from the inserter 120, 130, 136 by manual means or pushing the plunger 131 or other deploying device, and implanted on the posterior or outer surface 84 of the meniscal tissue 80 of the knee. The inserter 120, 130, 136 can be then withdrawn. At least one of ends 106a, 106b of the strand 106 can be pulled, causing the flexible member 102 to change to a second shape, as described above in connection with FIGS. 3, 4, 4A-7D. The thus-shaped flexible member 102 provides resistance against the outer meniscal surface 84, such that further tensioning the strand 106, causes the tear 82 to be reduced or closed. A slip knot, similar to the knot 156 illustrated in FIG. 20, and or another retaining device, such as a soft tissue anchor can be used to secure the strand 106 or the ends 106a, 106b to tissue.

Referring to FIGS. 6, 11, and 11A, the tubular inserter 130 can be used to implant multiple flexible members 102 on the posterior or other outer surface 84 of the meniscal tissue 80. The tubular inserter 130 can pre-loaded with multiple flexible members 102, which assume a first shape during loading and insertion, and which are coupled therebetween by the strand 106. After the first flexible member 102 is deployed from the inserter 130, as described above, in a first position on the outer surface 84, the inserter 130 can be withdrawn, re-inserted through the meniscal tear 82 and used to deploy a second flexible member 102 at a second position spaced apart from the first flexible member 102. After the last flexible member 102 is similarly deployed, the inserter 130 can be withdrawn, and the strand 106 tensioned by pulling one or both ends away from the tear 82, as illustrated in FIG. 6. Tensioning the strand 106 causes each of the flexible members 102 change to a second shape, thereby resisting further tensioning and causing the tear 82 to be reduced or closed.

The tubular inserter 130 can be similarly used to deploy one or more pipettes 150 independently, or with strands 154 and with or without one or more flexible members 102 for the configurations illustrated in FIGS. 16-20.

It will be appreciated that the soft-tissue repair assembly 100 of the present teachings provides an economically efficient, effective and versatile device for securing suture relative to soft tissue and repairing associated tears. Furthermore, the soft-tissue repair assembly 100 avoids or reduces tissue damage and relies on its rounded second shape for snug securing into tissue after implantation. Implantation can be facilitated by using an inserter according to the present teachings, and providing one or more flexible members 102 and connecting suture pre-loaded thereon. The new tissue repair techniques associated with the tissue repair assembly of the present teachings rely on existing surgeon skills and can be easily mastered.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:
1. A soft tissue repair device, comprising:
a first deformable anchor, the first deformable anchor deformable from a first shape to a second shape different than the first shape;
a first deformable vascularization conduit having a side wall and defining a plurality of perforations extending through the side wall;
a flexible strand having a first end and a second end and coupled to the first deformable anchor and the first deformable vascularization conduit, wherein upon pull- ing on at least one end of the flexible strand causes the first deformable anchor to deform from the first shape to the second shape; and
a first strand loop passing at least partially through a longitudinal bore of the first deformable anchor and having first and second loop ends extending outside the bore of the first deformable anchor.

2. The device of claim 1, wherein the flexible strand passes through the first and second loop ends of the first strand loop.

3. The device of claim 2, wherein the flexible strand extends through at least a portion of an inner bore of the first deformable vascularization conduit.

4. The device of claim 3, further comprising a second deformable anchor, the second deformable anchor deformable from a third shape to a fourth shape different from the third shape, wherein the flexible strand is coupled to the second deformable anchor.

5. The device of claim 4, further comprising a second deformable vascularization conduit having a side wall and defining a plurality of perforations extending through the side wall, wherein the flexible strand is coupled to the second deformable vascularization conduit.

6. The device of claim 4, wherein the first deformable vascularization conduit extends from a first end to a second end and the first anchor is positioned at the first end and the second anchor is positioned at the second end and the flexible strand extends through the side wall of the first deformable vascularization conduit.

7. A soft tissue repair device comprising:
a first deformable anchor defining an internal longitudinal bore and having first and second ends;
a first strand loop passing at least partially through the longitudinal bore of the first deformable anchor and having first and second loop ends extending outside the bore of the first deformable anchor;
a first tubular conduit for vascularization including an outer surface, a longitudinal inner bore extending between first and second open ends of the first tubular conduit and a plurality of perforations extending from the inner bore through the outer surface of the first tubular conduit; and
a flexible strand having first and second strand ends and coupled to the first and second loop ends of the first strand loop, the flexible strand extending substantially outside the first deformable anchor, the flexible strand passing through the inner bore of the first tubular conduit, such that pulling at least one of the first and second strand ends deforms the first deformable anchor from a first shape suitable for insertion through soft tissue to a second shape suitable for securely lodging the soft tissue repair device relative to the soft tissue.

8. The device of claim 7, wherein the first and second strand ends pass through the second end of the first tubular conduit.

9. The device of claim 7, wherein the first tubular conduit is deformable.

10. The device of claim 7, further comprising:
a second deformable anchor defining an internal longitudinal bore and having first and second ends; and
a second strand loop passing at least partially through the longitudinal bore of the second deformable anchor and having first and second loop ends extending outside the bore of the second deformable anchor; and wherein the flexible strand passes through the first and second loop ends of the second deformable anchor.

11. The device of claim 10, wherein the first and second ends of the flexible strand pass through an opening between the first and second ends of the tubular conduit.

12. The device of claim 7, further comprising:
a second tubular conduit for vascularization including an outer surface, a longitudinal inner bore extending between first and second open ends of the second tubular conduit and a plurality of perforations extending from the inner bore through the outer surface of the second tubular conduit;
a second deformable anchor defining an internal longitudinal bore and having first and second ends; and
a second strand loop passing at least partially through the longitudinal bore of the second deformable anchor and having first and second loop ends extending outside the bore of the second deformable anchor; and wherein the flexible strand passes through the first and second loop ends of the second deformable anchor and through the inner bore of the second tubular conduit.

13. The device of claim 12, wherein the first and second deformable anchors comprise woven material.

14. The device of claim 12, wherein the first and second tubular conduits are deformable.

15. The device of claim 14, wherein the first and second tubular conduits comprise woven material.

16. A soft tissue repair device comprising:
a first deformable anchor defining an internal longitudinal bore and having first and second ends;
a first strand loop passing at least partially through the longitudinal bore of the first deformable anchor and having first and second loop ends extending outside the bore of the first deformable anchor;
a second deformable anchor defining an internal longitudinal bore and having first and second ends;
a second strand loop passing at least partially through the longitudinal bore of the second deformable anchor and having first and second loop ends extending outside the bore of the second deformable anchor;
a first tubular conduit for vascularization including an outer surface and a longitudinal inner bore extending between first and second open ends of the first tubular conduit;
a second tubular conduit for vascularization including an outer surface and a longitudinal inner bore extending between first and second open ends of the tubular conduit; and
a flexible strand having first and second strand ends, the flexible strand passing a first time through the inner bore of the first tubular conduit, passing through the first and second loop ends of the first strand loop, passing a second time through the inner bore of the first tubular conduit, passing a first time through the inner bore of the second tubular conduit, passing through the first and second loop ends of the second strand loop and passing a second time through the inner bore of the second tubular conduit, such that pulling at least one of the first and second strand ends deforms the first and second deformable anchors from a first shape suitable for insertion through soft tissue to a second shape suitable for securely lodging the soft tissue repair device relative to the soft tissue.

17. The device of claim 16, wherein the first and second deformable anchors comprise woven material.

18. The device of claim 16, wherein the first and second tubular conduits are deformable.

19. The device of claim 18, wherein the first and second tubular conduits comprise woven material.

20. The device of claim 16, wherein each of the first and second tubular conduits has a plurality of perforations extending from the inner bore through the outer surface of the corresponding first and second tubular conduit.

21. A soft tissue repair device comprising:
a first deformable anchor defining an internal longitudinal bore and having first and second ends;
a first strand loop passing at least partially through the longitudinal bore of the first deformable anchor and having first and second loop ends extending outside the bore of the first deformable anchor;
a second deformable anchor defining an internal longitudinal bore and having first and second ends;
a second strand loop passing at least partially through the longitudinal bore of the second deformable anchor and having first and second loop ends extending outside the bore of the second deformable anchor;
a tubular conduit for vascularization, the tubular conduit including an outer surface and a longitudinal inner bore extending between first and second open ends of the tubular conduit; and
a flexible strand having first and second strand ends, the flexible strand passing a first time through the inner bore of the tubular conduit, passing through the first and second loop ends of the first strand loop, passing a second time through the inner bore of the tubular conduit and passing through the first and second loop ends of the second strand loop, such that pulling at least one of the first and second strand ends deforms the first and second deformable anchors from a first shape suitable for insertion through soft tissue to a second shape suitable for securely lodging the soft tissue repair device relative to the soft tissue.

22. The device of claim 21, wherein the first and second strand ends pass through an opening of the outer surface of the tubular conduit between the first and second ends of the tubular conduit.

23. The device of claim 21, wherein the tubular conduit is deformable.

24. The device of claim 21, wherein the tubular conduit is curved.

25. The device of claim 21, wherein the tubular conduit has a plurality of perforations extending from the inner bore through the outer surface of the tubular conduit.

* * * * *